(12) United States Patent
Wang et al.

(10) Patent No.: US 7,504,405 B2
(45) Date of Patent: Mar. 17, 2009

(54) MITOTIC KINESIN INHIBITORS

(75) Inventors: Weibo Wang, Moraga, CA (US); Ryan Constantine, Oakland, CA (US); Liana Lagniton, Berkeley, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 11/100,923

(22) Filed: Apr. 6, 2005

(65) Prior Publication Data

US 2005/0228002 A1    Oct. 13, 2005

Related U.S. Application Data

(60) Provisional application No. 60/560,235, filed on Apr. 6, 2004.

(51) Int. Cl.
C07D 487/04    (2006.01)
*A61K 31/519*    (2006.01)
A61P 35/00    (2006.01)

(52) U.S. Cl. .............. 514/259.4; 514/259.41; 514/269; 544/282; 544/319

(58) Field of Classification Search ............ 544/282, 544/319; 514/259.4, 259.41, 269
See application file for complete search history.

(56) References Cited

FOREIGN PATENT DOCUMENTS

| GB | 2 157 285 A | 10/1985 |
|---|---|---|
| WO | WO 03/049678 A2 | 6/2003 |
| WO | WO 03/094839 A2 | 11/2003 |
| WO | WO 03/103575 A2 | 12/2003 |
| WO | WO 2004/009036 A2 | 1/2004 |
| WO | WO 2004/064741 A2 | 8/2004 |
| WO | WO 2004/113335 A1 | 12/2004 |

OTHER PUBLICATIONS

Cecil Textbook of Medicine, edited by Bennet, J.C., and Plum F., 20th edition, vol. 1, 1004-1010, 1996.*
Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York, 1996, pp. 451 and 596.*
Hague et al. Cell Motil. Cytoskeleton, 58(1): 10-16, 2004.*
Mayer et al., Science 286: 971-974, 1999.*
Kapoor et al., J Cell Biol. 150:975-988, 2000.*

* cited by examiner

*Primary Examiner*—Venkataraman Balasubramanian
(74) *Attorney, Agent, or Firm*—Vinit Kathardekar; Lorna Tanner

(57) ABSTRACT

The present invention relates to compounds that are useful for treating cellular proliferative diseases, for treating disorders mediated, at least in part, by KSP, and for inhibiting KSP. The invention also related to pharmaceutical compositions comprising such compounds, methods of treating cancer by the administration of such compositions, and processes for the preparation of the compounds. Compounds of the invention have the following formula:

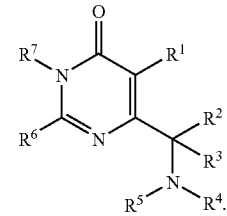

18 Claims, No Drawings

MITOTIC KINESIN INHIBITORS

CROSS-REFERENCE TO RELATED APPLICATIONS

This application claims the benefit under 35 U.S.C. §119 (e) of U.S. Application Ser. No. 60/560,235, filed Apr. 6, 2004, which is hereby incorporated by reference in its entirety.

FIELD OF THE INVENTION

The present invention relates to compounds that are useful in treating disorders mediated, at least in part, by KSP, and pharmaceutically acceptable salts, esters or prodrugs thereof, compositions of these compounds together with pharmaceutically acceptable carriers.

BACKGROUND OF THE INVENTION

Kinesins are motor proteins that use adenosine triphosphate to bind to microtubules and generate mechanical force. Kinesins are characterized by a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmic reticulum. Several KRPs interact with the microtubules of the mitotic spindle or with the chromosomes directly and appear to play a pivotal role during the mitotic stages of the cell cycle. These mitotic KRPs are of particular interest for the development of cancer therapeutics.

Kinesin spindle protein (KSP) (also known as Eg5, HsEg5, KNSL1, or KIFII) is one of several kinesin-like motor proteins that are localized to the mitotic spindle and known to be required for formation and/or function of the bipolar mitotic spindle.

In 1995, the depletion of KSP using an antibody directed against the C-terminus of KSP was shown to arrest HeLa cells in mitosis with monoastral microtubule arrays (Blangy et al., Cell 83:1159-1169, 1995). Mutations in bimC and cut7 genes, which are considered to be homologues of KSP, cause failure in centrosome separation in *Aspergillus nidulans* (Enos, A. P., and N. R. Morris, Cell 60:1019-1027, 1990) and *Schizosaccharomyces pombe* (Hagan, I., and M. Yanagida, Nature 347:563-566, 1990). Treatment of cells with either ATRA (all trans-retinoic acid), which reduces KSP expression on the protein level, or depletion of KSP using antisense oligonucleotides revealed a significant growth inhibition in DAN-G pancreatic carcinoma cells indicating that KSP might be involved in the antiproliferative action of all trans-retinoic acid (Kaiser, A., et al., J. Biol. Chem. 274, 18925-18931, 1999). Interestingly, the *Xenopus laevis* Aurora-related protein kinase pEg2 was shown to associate and phosphorylate XlEg5 (Giet, R., et al., J. Biol. Chem. 274:15005-15013, 1999). Potential substrates of Aurora-related kinases are of particular interest for cancer drug development. For example, Aurora 1 and 2 kinases are overexpressed on the protein and RNA level and the genes are amplified in colon cancer patients.

The first cell permeable small molecule inhibitor for KSP, "monastrol," was shown to arrest cells with monopolar spindles without affecting microtubule polymerization as do conventional chemotherapeutics such as taxanes and vinca alkaloids (Mayer, T. U., et al., Science 286:971-974, 1999). Monastrol was identified as an inhibitor in phenotype-based screens and it was suggested that this compound may serve as a lead for the development of anticancer drugs. The inhibition was determined not to be competitive in respect to adenosine triphosphate and to be rapidly reversible (DeBonis, S., et al., Biochemistry 42:338-349, 2003; Kapoor, T. M., et al., J. Cell Biol. 150:975-988, 2000).

In light of the importance of improved chemotherapeutics, there is a need for KSP inhibitors that are effective in vivo inhibitors of KSP and KSP-related proteins.

SUMMARY OF THE INVENTION

The present invention relates to compounds that are useful for treating disorders mediated, at least in part, by KSP, and for inhibiting KSP. The present invention provides small molecule inhibitors of KSP, pharmaceutical compositions containing such inhibitors, methods of treating patients with such pharmaceutical compositions, and methods of preparing such pharmaceutical compositions and inhibitors. The inhibitors can be used in the prophylaxis and/or treatment of disorders mediated, at least in part, by KSP, such as cellular proliferative diseases or cancer.

The compounds of the invention may be illustrated by the formula I:

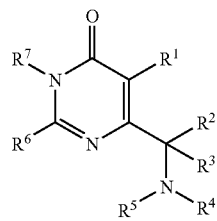

I or a pharmaceutically acceptable salt, stereoisomer or prodrug thereof, wherein:

$R^1$ is selected from the group consisting of alkyl, alkenyl, alkynyl, aryl, heterocyclyl, halo, cyano, nitro, carboxy, hydroxy, alkoxy, aryloxy, heterocyclyloxy, aminocarbonyl, aminocarbonyloxy, alkylcarbonyloxy, arylcarbonyloxy, heterocyclylcarbonyloxy, alkoxycarbonyl, aryloxycarbonyl, heterocyclyloxycarbonyl, amino, alkylcarbonylamino, arylcarbonylamino, heterocyclylcarbonylamino, alkoxycarbonylamino, aryloxycarbonylamino, heterocyclyloxycarbonylamino, alkylsulfonylamino, arylsulfonylamino, heterocyclylsulfonylamino, aminosulfonyl, alkylsulfonyl, arylsulfonyl, and heterocyclylsulfonyl;

$R^2$ is selected from the group consisting of hydrogen, alkyl, alkenyl, alkynyl, aryl, heterocyclyl, carboxy, alkoxycarbonyl, aryloxycarbonyl, heterocyclyloxycarbonyl, and aminocarbonyl;

$R^3$ is selected from the group consisting of alkyl, alkenyl, alkynyl, aryl, and heterocyclyl, or $R^2$ and $R^3$, together with the carbon atom to which they are attached can form a carbocyclic or heterocyclic ring, having from 3 to 8 ring atoms, wherein from 1 to 3 ring atoms of the heterocyclic ring are selected from the group consisting of N, O and S;

$R^4$ is selected from the group consisting of hydrogen, alkyl, aryl, and heterocyclyl;

$R^5$ is selected from the group consisting of hydrogen, alkyl, aryl, heterocyclyl, alkoxycarbonyl, aryloxycarbonyl, heterocyclyloxycarbonyl, aminocarbonyl, alkylcarbonyl, arylcarbonyl, heterocyclylcarbonyl, alkylsulfonyl, arylsulfonyl, and heterocyclylsulfonyl;

$R^6$ is selected from the group consisting of hydrogen, alkyl, aryl, heterocyclyl, hydroxy, alkoxy, aryloxy, heterocyclyloxy, amino, alkylsulfonyl, arylsulfonyl, and heterocyclylsulfonyl, alkylcarbonyloxy, arylcarbonyloxy, heterocyclylcarbonyloxy, alkoxycarbonyl, aryloxycarbonyl, heterocyclyloxycarbonyl, alkoxycarbonylamino, aryloxycarbonylamino, heterocyclyloxycarbonylamino, alkylcarbonylamino, arylcarbonylamino, heterocyclylcarbonylamino, aminocarbonyloxy, alkylsulfonylamino, arylsulfonylamino, heterocyclylsulfonylamino, and aminosulfonyl; and $R^7$ is selected from the group consisting of hydrogen, alkyl, aryl, and heterocyclyl, or $R^6$ and $R^7$, can be taken together with the atoms to which they are attached to form a heterocyclic ring, having 5 to 8 ring atoms, wherein from 1 to 3 ring atoms of the heterocyclic ring are selected from the group consisting of N, O and S.

In one embodiment, the compounds of this invention are illustrated by a compound of formula II:

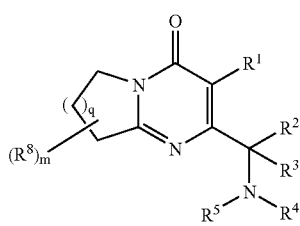

II or a pharmaceutically acceptable salt, stereoisomer or prodrug thereof, wherein $R^1$, $R^2$, $R^3$, $R^4$, and $R^5$ are defined as above;

m is 0, 1, 2, or 3;

q is 1, 2, or 3; and and $R^8$ is selected from the group consisting of alkyl, aryl, and heterocyclyl.

Formula II also includes the tautomer of formula II, illustrated as formula II-a:

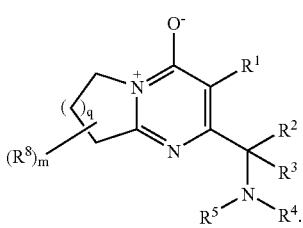

II-a

In another embodiment, the compounds of this invention are illustrated by a compound of formula III:

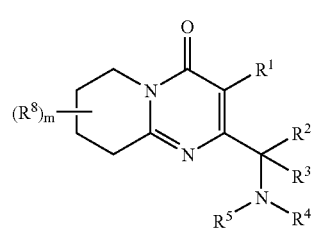

III or a pharmaceutically acceptable salt, stereoisomer or prodrug thereof, wherein:

$R^1$, $R^2$, $R^3$, $R^4$, $R^5$ are as defined herein;

m is 0, 1, 2, or 3; and $R^8$ is selected from the group consisting of alkyl, aryl, and heterocyclyl.

In yet another embodiment, compounds of this invention are illustrated by a compound of formula IV:

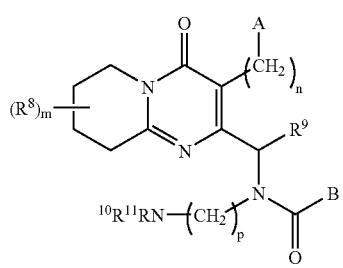

IV wherein A and B are independently selected from the group consisting of aryl, heteroaryl, heterocyclyl, cycloalkyl, all of which may be substituted with 1 to 4 substituents selected from the group consisting of alkyl, alkoxy, halo, hydroxy, and nitro;

n is 1, 2, or 3;

m is 0, 1, 2, or 3;

p is 1, 2, 3 or 4;

$R^8$ is alkyl, aryl, and heterocyclyl;

$R^9$ is $C_2$ to $C_3$ alkyl;

$R^{10}$ and $R^{11}$ are independently selected from the group consisting of hydrogen and $C_1$ to $C_4$ alkyl.

PREFERRED EMBODIMENTS

In one embodiment, $R^1$ is alkyl. In another embodiment, $R^1$ is alkyl substituted with aryl or heterocyclyl. In yet another embodiment, $R^1$ is benzyl.

In one embodiment, $R^2$ is H.

In one embodiment, $R^3$ is alkyl, alkenyl, alkynyl, aryl, or heterocyclyl. In another embodiment, $R^3$ is ethyl, isopropyl, cyclopropyl, phenyl, thienyl, or pyridinyl. In yet another embodiment, $R^3$ is ethyl or isopropyl.

In one embodiment, $R^4$ is alkyl. In another embodiment, $R^4$ is 2-aminoethyl, 3-aminopropyl, 4-aminobutyl, 3-(methylamino)propyl, or 3-(ethylamino)propyl. In yet another embodiment, $R^4$ is 3-aminopropyl, 3-(methylamino)propyl, or 3-(ethylamino)propyl.

In one embodiment, $R^5$ is arylcarbonyl or heterocyclylcarbonyl. In another embodiment, $R^5$ is benzoyl, 4-chlorobenzoyl, 4-bromobenzoyl, 4-methylbenzoyl, 3-fluoro-4-methylbenzoyl, or 4-trifluoromethylbenzoyl. In yet another embodiment, $R^5$ is 4-bromobenzoyl, 3-fluoro-4-methylbenzoyl, or 4-methylbenzoyl.

In one embodiment, $R^6$ and $R^7$, together with the atoms pendent thereto form a heterocyclic ring. In another embodiment, the $R^6$ and $R^7$ together with the atoms pendent thereto join to form 4-oxo-6,7,8,9-tetrahydro-4H-pyrido[1,2-a]pyrimidin-2-yl.

In one embodiment, m is 0.

In one embodiment, when m is 1, 2, or 3, $R^8$ is alkyl. In another embodiment, $R^8$ is methyl.

In one embodiment, m is 1. In another embodiment, q is 2. In yet another embodiment p is 3. In still yet another embodiment, n is 1.

In one embodiment, $R^9$ is ethyl, isopropyl, cyclopropyl, or propyl. In yet another embodiment, $R^9$ is ethyl or isopropyl.

In one embodiment, A is aryl. In another embodiment, A is phenyl.

In one embodiment, B is aryl. In another embodiment, B is aryl substituted with alkyl and/or halo. In yet another embodiment, B is phenyl substituted with methyl, fluoro, and/or bromo.

In one embodiment, both $R^{10}$ and $R^{11}$ are both hydrogen. In another embodiment, one of $R^{10}$ or $R^{11}$ is hydrogen and the other is alkyl. In yet another embodiment, one of $R^{10}$ or $R^{11}$ is hydrogen and the other is ethyl or methyl.

Compounds within the scope of the invention are exemplified by those set forth in Table 1 as follows.

Specific examples of the compounds of the invention include:

N-(3-aminopropyl)-N-[1-(3-benzyl-4-oxo-6,7,8,9-tetrahydro-4H-pyrido[1,2-a]pyrimidin-2-yl)propyl]-4-bromobenzamide;

N-(3-aminopropyl)-N-[1-(3-benzyl-4-oxo-6,7,8,9-tetrahydro-4H-pyrido[1,2-a]pyrimidin-2-yl)-2-methylpropyl]-4-methylbenzamide;

N-(3-aminopropyl)-N-[1-(3-benzyl-8-methyl-4-oxo-6,7,8,9-tetrahydro-4H-pyrido [1,2-a]pyrimidin-2-yl)propyl]-4-methylbenzamide;

N-(3-aminopropyl)-N-[1-(3-benzyl-4-oxo-6,7,8,9-tetrahydro-4H-pyrido[1,2-a]pyrimidin-2-yl)-2-methylpropyl]-3-fluoro-4-methylbenzamide;

N-(3-ethylaminopropyl)-N-[1-(3-benzyl-4-oxo-6,7,8,9-tetrahydro-4H-pyrido[1,2-a]pyrimidin-2-yl)-2-methylpropyl]-4-methylbenzamide;

N-(3-ethylaminopropyl)-N-[1-(3-benzyl-4-oxo-6,7,8,9-tetrahydro-4H-pyrido[1,2-a]pyrimidin-2-yl)-2-methylpropyl]-3-fluoro-4-methylbenzamide; and N-(3-methylaminopropyl)-N-[1-(3-benzyl-4-oxo-6,7,8,9-tetrahydro-4H-pyrido[1,2-a]pyrimidin-2-yl)-2-methylpropyl]-4-methylbenzamide.

Compounds of this invention may exhibit stereoisomerism by virtue of the presence of one or more asymmetric or chiral centers in the compounds. The present invention contemplates the various stereoisomers and mixtures thereof. Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, single enantiomer, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," Pure Appl. Chem. 45:13 30, 1976. Desired enantiomers can be obtained by chiral synthesis from commercially available chiral starting materials by methods well known in the art, or may be obtained from mixtures of the enantiomers by separating the desired enantiomer by using known techniques.

TABLE 1

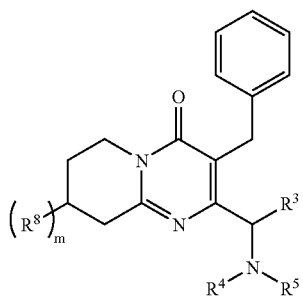

| No. | $R^1$ | $R^3$ | $R^4$ | $R^5$ | m | $R^8$ |
|---|---|---|---|---|---|---|
| 1 | —CH$_2$Ph | —CH$_2$CH$_3$ | —(CH$_2$)$_3$NH$_2$ | —C(O)-4-Br-Ph | 0 | H |
| 2 | —CH$_2$Ph | —CH(CH$_3$)(CH$_3$) | —(CH$_2$)$_3$NH$_2$ | —C(O)-4-CH$_3$-Ph | 0 | H |
| 3 | —CH$_2$Ph | —CH$_2$CH$_3$ | —(CH$_2$)$_3$NH$_2$ | —C(O)-4-CH$_3$-Ph | 1 | —CH$_3$ |
| 4 | —CH$_2$Ph | —CH(CH$_3$)(CH$_3$) | —(CH$_2$)$_3$NH$_2$ | —C(O)-3-F-4-CH$_3$-Ph | 0 | H |
| 5 | —CH$_2$Ph | —CH(CH$_3$)(CH$_3$) | —(CH$_2$)$_3$NHCH$_2$CH$_3$ | —C(O)-4-CH$_3$-Ph | 0 | H |
| 6 | —CH$_2$Ph | —CH(CH$_3$)(CH$_3$) | —(CH$_2$)$_3$NHCH$_2$CH$_3$ | —C(O)-3-F-4-CH$_3$-Ph | 0 | H |
| 7 | —CH$_2$Ph | —CH(CH$_3$)(CH$_3$) | —(CH$_2$)$_3$NHCH$_3$ | —C(O)-4-CH$_3$-Ph | 0 | H |

Compounds of this invention may also exhibit geometrical isomerism. Geometric isomers include the cis and trans forms of compounds of the invention having alkenyl or alkenylenyl moieties. The present invention comprises the individual geometrical isomers and stereoisomers and mixtures thereof.

DETAILED DESCRIPTION OF THE INVENTION

A. Definitions

The following definitions are provided to better understand the invention and are used throughout this application.

It is to be understood that the terminology used herein is for the purpose of describing particular embodiments only and is not intended to limit the scope the present invention. It must also be understood that as used herein and in the claims, the singular forms "a," "and" and "the" include plural referents unless the context clearly dictates otherwise. In this specification and in the claims which follow, reference will be made to a number of terms which shall be defined to have the following meanings.

Generally, reference to a certain element such as hydrogen or H is meant to include all isotopes of that element. For example, if an R group is defined to include hydrogen or H, it also includes deuterium and tritium.

The term "alkyl" refers to both "unsubstituted alkyl" and "substituted alkyl" groups.

The phrase "unsubstituted alkyl" refers to monovalent, aliphatic hydrocarbyl groups and includes straight chain or branched saturated radicals having from 1 to 20 carbon atoms. The "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_3$)CH(CH$_3$)CH(CH$_3$)CH(CH$_3$)(CH$_2$CH$_3$), and others.

The phrase also includes cyclic alkyl groups also referred to herein as "cycloalkyl." Such groups may have single or multiple cyclic rings can include, by way of example only, cyclopropyl, cyclobutyl, cyclopentyl, cyclohexyl, cycloheptyl, and cyclooctyl and such rings substituted with straight and branched chain alkyl groups as defined above.

Thus the phrase "alkyl" includes primary alkyl groups, secondary alkyl groups, and tertiary alkyl groups. Preferred alkyl groups include straight and branched chain alkyl groups having 1 to 12 carbon atoms and cyclic alkyl groups having 3 to 12 carbon atoms. Further preferred alkyl groups include straight and branched chain alkyl groups having 1 to 6 carbon atoms and cyclic alkyl groups having 3 to 8 carbon atoms. "C$_1$-C$_6$ alkyl" refers to a hydrocarbon radical straight, branched or cyclic, containing from 1 to 6 carbon atoms.

The phrase "substituted alkyl" refers to an alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups (—SO$_2$), sulfonyl groups (—SO$_2$—), and sulfoxide groups (—S(=O)—); a nitrogen atom in groups such as amines, amides, alkylamines, dialkylamines, arylamines, alkylarylamines, diarylamines, N-oxides (N→O), imides (—C(=O)—NH—C(=O)—), and enamines (—C=C—NH$_2$); a silicon atom in groups such as in trialkylsilyl groups (—Si(alkyl)$_3$ where each alkyl group can be the same or different), dialkylarylsilyl groups (—Si(alkyl)$_2$(aryl), where each alkyl group can be the same or different), alkyldiarylsilyl groups (—Si(alkyl)(aryl)$_2$, where each aryl group can be the same or different), and triarylsilyl groups (—Si(aryl)$_3$ where each aryl group can be the same or different); and other heteroatoms in various other groups.

Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines (—C=N—R), oximes (—C=N—OH), hydrazones (—C=NNH$_2$), and nitriles (—C≡N). Substituted alkyl groups further include alkyl groups in which one or more bonds to a carbon(s) or hydrogen(s) atoms is replaced by a bond to an aryl, heteroaryl, heterocyclyl, or cycloalkyl group. Preferred substituted alkyl groups include, among others, alkyl groups in which one or more bonds to a carbon or hydrogen atom is/are replaced by one or more bonds to fluoro, chloro, or bromo group. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Other preferred substituted alkyl groups include alkyl groups that have an amine, or a substituted or unsubstituted alkylamino, dialkylamino, arylamino, (alkyl)(aryl)amino, diarylamino, heterocyclylamino, diheterocyclylamino, (alkyl)(heterocyclyl)amino, or (aryl)(heterocyclyl)amino group. Still other preferred substituted alkyl groups include those in which one or more bonds to a carbon(s) or hydrogen(s) atoms is replaced by a bond to an aryl, heteroaryl, heterocyclyl, or cycloalkyl group. Examples of substituted alkyl are: —(CH$_2$)$_3$NH$_2$, —(CH$_2$)$_3$NH(CH$_3$), —(CH$_2$)$_3$NH(CH$_3$)$_2$, —CH$_2$C(=CH$_2$)CH$_2$NH$_2$, —CH$_2$C(=O)CH$_2$NH$_2$, —CH$_2$S(=O)$_2$CH$_3$, —CH$_2$OCH$_2$NH$_2$, and —CO$_2$H. Examples of substituents of substituted alkyl include but are not limited to: —CH$_2$OH, —OH, —OCH$_3$, —OC$_2$H$_5$, —OCF$_3$, —OC(=O)CH$_3$, —OC(=O)NH$_2$, —OC(=O)N(CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(=O)OCH$_3$, —NHSO$_2$CH$_3$, —SO$_2$CH$_3$, —SO$_2$NH$_2$, and halo.

"Cycloalkyl" refers to a mono- or polycyclic alkyl groups in which all ring atoms are carbon. Typical cycloalkyl substituents have from 3 to 8 ring atoms. When used in connection with cycloalkyl substituents, the term "polycyclic" refers herein to fused and non-fused alkyl cyclic structures.

The phrase "alkenyl" refers to both "unsubstituted alkenyl" and "substituted alkenyl" groups.

The phrase "unsubstituted alkenyl" refers to straight and branched chain and cyclic groups (but not aromatic) such as those described with respect to unsubstituted alkyl groups as defined above, except that at least one double bond exists between two carbon atoms. Examples include, but are not limited to vinyl, —CH=C(H)(CH$_3$), —CH=C(CH$_3$)$_2$, —C(CH$_3$)=C(H)$_2$, —C(CH$_3$)=C(H)(CH$_3$), —C(CH$_2$CH$_3$)

=CH$_2$, cyclohexenyl, cyclopentenyl, cyclohexadienyl, butadienyl, pentadienyl, and hexadienyl among others. "C$_2$-C$_6$ alkenyl" means an alkenyl radical having from 2 to 6 atoms.

The phrase "substituted alkenyl" has the same meaning with respect to alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "alkynyl" refers to both "unsubstituted alkynyl" and "substituted alkynyl" groups.

The phrase "unsubstituted alkynyl" refers to straight and branched chain groups such as those described with respect to unsubstituted alkyl groups as defined above, except that at least one triple bond exists between two carbon atoms. Examples include, but are not limited to, —C≡C(H), —C≡C(CH$_3$), —C≡C(CH$_2$CH$_3$), —C(H$_2$)C≡C(H), —C(H)$_2$C≡C(CH$_3$), and —C(H)$_2$C≡C(CH$_2$CH$_3$) among others. "C$_2$-C$_6$ alkynyl" means an alkynyl radical having from 2 to 6 carbon atoms.

The phrase "substituted alkynyl" has the same meaning with respect to alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "aryl" refers to both "unsubstituted aryl" and "substituted aryl" groups.

The phrase "unsubstituted aryl" refers to monocyclic and polycyclic aromatic groups having from 6 to 14 carbon atoms. "Unsubstituted aryl" refers to aryl groups that do not contain heteroatoms. Thus the phrase includes, but is not limited to, groups such as phenyl, biphenyl, anthracenyl, naphthenyl by way of example. A preferred unsubstituted aryl group is phenyl. Unsubstituted aryl groups may be bonded to one or more carbon atom(s), oxygen atom(s), nitrogen atom(s), and/or sulfur atom(s) in the parent compound outside of the ring structure.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

Preferred substituents include straight and branched chain alkyl groups, —CH$_3$, —C$_2$H$_5$, —CH$_2$OH, —OH, —OCH$_3$, —OC$_2$H$_5$, —OCF$_3$, —OC(=O)CH$_3$, —OC(=O)NH$_2$, —OC(=O)N(CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(=O)OCH$_3$, —NHSO$_2$CH$_3$, —SO$_2$CH$_3$, —SO$_2$NH$_2$, and halo.

"Aralkyl" or "arylalkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

The phrase "carbocyclic" refers to both "unsubstituted carbocyclic" and "substituted carbocyclic" groups.

The phrase "unsubstituted carbocyclic" refers to both aromatic and nonaromatic ring compounds including monocyclic, bicyclic, and polycyclic ring compounds such as cycloalkyl or aryl groups.

The phrase "heterocyclyl" refers to both "unsubstituted heterocyclyl" and "substituted heterocyclyl" groups.

The phrase "unsubstituted heterocyclyl" refers to both aromatic and nonaromatic ring compounds including monocyclic, bicyclic, and polycyclic ring compounds such as, but not limited to, quinuclidinyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups.

Examples of heterocyclyl groups include, but are not limited to, unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl.

Heterocyclyl groups also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to a unsubstituted heterocyclyl group as defined above in which one or more of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

The phrase "heteroaryl" refers to both "unsubstituted heteroaryl" and "substituted heteroaryl" groups.

The term "unsubstituted heteroaryl", as used herein, refers to a cyclic or bicyclic aromatic radical having from 5 to 10 ring atoms in each ring of which one atom of the cyclic or bicyclic ring is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and naphthyridinyl, and the like.

The term "substituted heteroaryl" refers to a unsubstituted heteroaryl group as defined above in which one or more of the ring members is bonded to a non-hydrogen atom such as described above with respect to substituted alkyl groups and substituted aryl groups. Preferred substituents include straight and branched chain alkyl groups —CH$_3$, —C$_2$H$_5$, —CH$_2$OH, —OH, —OCH$_3$, —OC$_2$H$_5$, —OCF$_3$, —OC(=O)CH$_3$, —OC(=O)NH$_2$, —OC(=O)N(CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(=O)OCH$_3$, —NHSO$_2$CH$_3$, —SO$_2$CH$_3$, —SO$_2$NH$_2$, and halo.

The term "biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)phenyl]acetamide, 1,4-diphenylbenzene, N-[4-(2-phenylethynyl)phenyl]-2-[benzylamino]acetamide, 2-amino-N-[4-(2-phenylethynyl)phenyl]propanamide, 2-amino-N-[4-(2-phenylethynyl)phenyl]acetamide, 2-(cyclopropylamino)-N-[4-(2-phenylethynyl)phenyl]acetamide, 2-(ethylamino)-N-[4-(2-phenylethynyl)phenyl]acetamide, 2-[(2-methylpropyl)amino]-N-[4-(2-phenylethynyl)phenyl]acetamide, 5-phenyl-2H-benzo[d]1,3-dioxolene, 2-chloro-1-methoxy-4-phenylbenzene, 2-[(imidazolylmethyl)amino]-N-[4-(2-phenylethynyl)phenyl]acetamide, 4-phenyl-1-phenoxybenzene, N-(2-aminoethyl)[4-(2-phenylethynyl)phenyl]carboxamide, 2-{[(4-fluorophenyl)methyl]amino}-N-[4-(2-phenylethynyl)phenyl]acetamide, 2-{[(4-methylphenyl)methyl]amino}-N-[4-(2-phenylethynyl)phenyl]acetamide, 4-phenyl-1-(trifluoromethyl)benzene, 1-butyl-4-phenylbenzene, 2-(cyclohexylamino)-N-[4-(2-phenylethynyl)phenyl]acetamide, 2-(ethylmethylamino)-N-[4-(2-phenylethynyl)phenyl]acetamide, 2-(butylamino)-N-[4-(2-phenylethynyl)phenyl]acetamide, N-[4-(2-phenylethynyl)phenyl]-2-(4-pyridylamino)acetamide, N-[4-(2-phenylethynyl)phenyl]-2-(quinuclidin-3-ylamino)acetamide, N-[4-(2-phenylethynyl)phenyl]pyrrolidin-2-ylcarboxamide, 2-amino-3-methyl-N-[4-(2-phenylethynyl)phenyl]butanamide, 4-(4-phenylbuta-1,3-diynyl)phenylamine, 2-(dimethylamino)-N-[4-(4-phenylbuta-1,3-diynyl)phenyl]acetamide, 2-(ethylamino)-N-[4-(4-phenylbuta-1,3-diynyl)phenyl]acetamide, 4-ethyl-1-phenylbenzene, 1-[4-(2-phenylethynyl)phenyl]ethan-1-one, N-(1-carbamoyl-2-hydroxypropyl) [4-(4-phenylbuta-1,3-diynyl)phenyl]carboxamide, N-[4-(2-phenylethynyl)phenyl]propanamide, 4-methoxyphenyl phenyl ketone, phenyl-N-benzamide, (tert-butoxy)-N-[(4-phenylphenyl)methyl]carboxamide, 2-(3-phenylphenoxy)ethanehydroxamic acid, 3-phenylphenyl propanoate, 1-(4-ethoxyphenyl)-4-methoxybenzene, and [4-(2-phenylethynyl)phenyl]pyrrole.

The term "heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenylethynyl)-1,3-dihydropyrimidine-2,4-dione, 4-phenyl-1,2,3-thiadiazole, 2-(2-phenylethynyl)pyrazine, 2-phenylthiophene, phenylimidazole, 3-(2-piperazinylphenyl)furan, 3-(2,4-dichlorophenyl)-4-methylpyrrole, and the like. Preferred optionally substituted heteroarylaryl groups include: 5-(2-phenylethynyl)pyrimidine-2-ylamine, 1-methoxy-4-(2-thienyl)benzene, 1-methoxy-3-(2-thienyl)benzene, 5-methyl-2-phenylpyridine, 5-methyl-3-phenylisoxazole, 2-[3-(trifluoromethyl)phenyl]furan, 3-fluoro-5-(2-furyl)-2-methoxy-1-prop-2-enylbenzene, (hydroxyimino)(5-phenyl(2-thienyl))methane, 5-[(4-methylpiperazinyl)methyl]-2-phenylthiophene, 2-(4-ethylphenyl)thiophene, 4-methylthio-1-(2-thienyl)benzene, 2-(3-nitrophenyl)thiophene, (tert-butoxy)-N-[(5-phenyl(3-pyridyl))methyl]carboxamide, hydroxy-N-[(5-phenyl(3-pyridyl))methyl]amide, 2-(phenylmethylthio)pyridine, and benzylimidazole.

The term "heteroarylheteroaryl" refers to a biaryl group where both of the aryl groups is a heteroaryl group. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl)furan, diethyl(3-pyrazin-2-yl(4-pyridyl))amine, and dimethyl {2-[2-(5-methylpyrazin-2-yl)ethynyl](4-pyridyl)}amine.

The substitution group can itself be substituted. The group substituted onto the substitution group can be carboxyl, halo; nitro, amino, cyano, hydroxy, alkyl, alkoxy, aminocarbonyl, —SR$^a$, thioamido, —SO$_3$H, —SO$_2$R$^a$ or cycloalkyl, where R$^a$ is typically hydrogen, hydroxyl or alkyl.

When the substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituents can be straight chain, branched or cyclic arrangements of covalently bonded carbon or heteroatoms.

"Halogen" or "halo" refers to chloro, bromo, fluoro, and iodo groups. The term "haloalkyl" refers to an alkyl radical substituted with one or more halogen atoms. The term "haloalkoxy" refers to an alkoxy radical substituted with one or more halogen atoms.

"Cyano" refers to —CN.

"Nitro" refers to —NO$_2$.

"Carboxy" or "carboxyl" refers to —C(=O)—OH.

"Hydroxy" or "hydroxyl" refers to —OH.

"Alkoxy" refers to —O-alkyl. Representative examples of alkoxy groups include methoxy, ethoxy, t-butoxy, trifluoromethoxy, and the like.

"Aryloxy" refers to —O-aryl. Representative examples of aryloxy groups include phenoxy, naphthoxy, and the like.

"Heterocyclyloxy" refers to —O-heterocyclyl.

"Carbonyl" refers to the divalent group —C(=O)—.

"Ester" refers to the divalent group —C(=O)O—.

"Thiol" refers to the group —SH.

"Alkylsulfides" or "alkylthio" refers to the group —S-alkyl.

"Arylsulfides" or "arylthio" refers to the group —S-aryl.

"Alkylcarbonyloxy" refers herein to the group —OC(=O) alkyl.

"Arylcarbonyloxy" refers herein to the group —OC(=O) aryl.

"Heterocyclylcarbonyloxy" refers herein to the group —OC(=O)-heterocyclyl.

The phrase "amino" refers to both "unsubstituted amino" and "substituted amino" groups.

"Unsubstituted amino" refers herein to the group —NH$_2$.

"Substituted amino" or "substituted amine" refers herein to the group —NR$^b$R$^b$ where each R$^b$ is independently selected from H, alkyl, aryl, heteroaryl or heterocyclyl. The term "alkylamino" refers herein to the group —NR$^c$R$^d$ wherein R$^c$ is alkyl and R$^d$ is H or alkyl. The term "dialkyl amino" refers to the group —NR$^c$R$^c$ wherein each R$^c$ can be the same or different alkyl. The term "arylamino" refers herein to the group —NR$^e$R$^f$ where R$^e$ is aryl and R$^f$ is hydrogen, alkyl, aryl, heteroaryl, or heterocyclyl. The term "alkylarylamino" refers to the group —NR$^c$R$^e$ wherein R$^c$ is alkyl and R$^e$ is aryl. The term "diarylamino" refers to the group —NR$^e$R$^e$ wherein each R$^e$ can be the same or different aryl. The term "heterocyclylamino" refers to the group —NR$^b$R$^g$ wherein R$^b$ is as defined herein and R$^g$ is heterocyclyl. The term "diheterocyclylamino" refers to the group —NR$^g$R$^g$, wherein each R$^g$ is the same or different heterocylyl. The term "(alkyl)(heterocylyl)amino" refers to the group —NR$^c$R$^g$ where R$^c$ and R$^g$ are as defined herein. The term "(aryl)(heterocyclyl)amino" refers to the group —NR$^e$R$^g$, wherein R$^e$ and R$^g$ are as defined herein.

"Aminocarbonyl" or "amide" refers herein to the group —C(O)—NH$_2$ or —C(O)—NR$^b$R$^b$ where each R$^b$ is independently selected from H, alkyl, aryl, heteroaryl or heterocyclyl. The term "alkylaminocarbonyl" refers herein to the amide —C(O)—NR$^c$R$^d$ wherein R$^c$ is alkyl and R$^d$ is H or alkyl. The term "arylaminocarbonyl" refers herein to the amide —C(O)—NR$^e$R$^f$ where R$^e$ is aryl and R$^f$ is hydrogen, alkyl, aryl, heteroaryl, or heterocyclyl. Representative aminocarbonyl groups include, for example, those shown below. These aminocarbonyl group can be further substituted as will be apparent to those having skill in the organic and medicinal chemistry arts in conjunction with the disclosure herein.

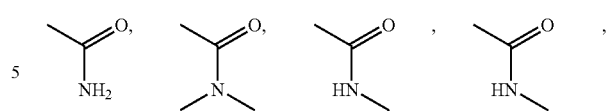

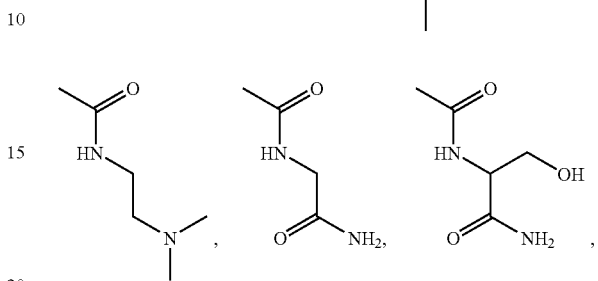

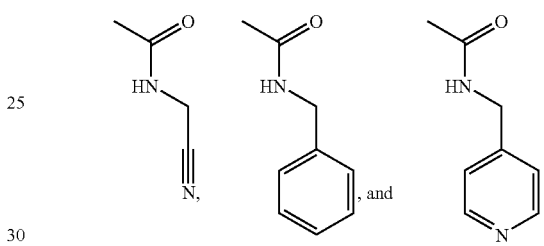

"Aminocarbonyloxy" refers to the group —O—C(=O)-amino.

"Aminooxycarbonyl" refers to the group —C(=O)—O-amino.

"Alkylcarbonyl" refers to the group —C(O)-alkyl.

"Arylcarbonyl" refers to the group —C(=O)-aryl.

"Heterocyclylcarbonyl" refers to the group —C(=O)-heterocyclyl.

"Alkoxycarbonyl" or "carboxylalkyl" refers to the group —C(=O)—O-alkyl. Representative alkoxycarbonyl groups include, for example, those shown below. These alkoxycarbonyl groups can be further substituted as will be apparent to those having skill in the organic and medicinal chemistry arts in conjunction with the disclosure herein.

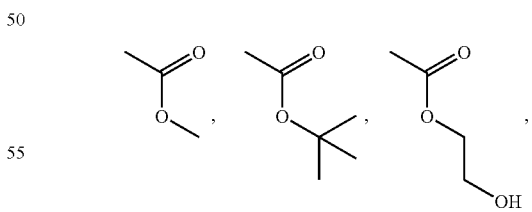

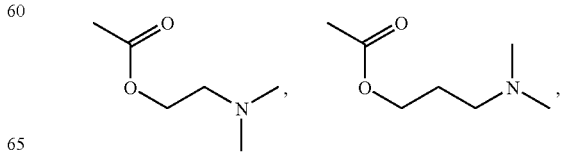

-continued

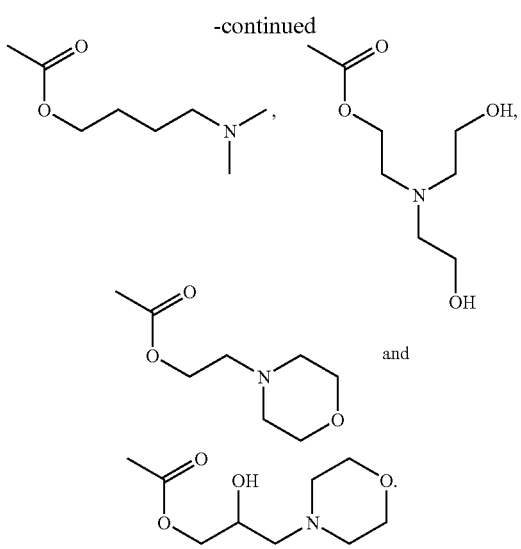

"Aryloxycarbonyl" refers to —C(═O)O-aryl.

"Heterocyclyloxycarbonyl" refers to —C(═O)—O-heterocyclyl.

"Alkylcarbonylamino" refers herein to —N(R$^b$)C(═O_alkyl wherein R$^b$ is as defined above. Representative alkylcarbonylamino groups include, for example, —NHC(═O)CH$_3$, —NHC(═O)CH$_2$CH$_3$, —NHC(═O)CH$_2$NH(CH$_3$), —NHC(═O)CH$_2$N(CH$_3$)$_2$, or —NHC(═O)(CH$_2$)$_3$OH. These groups can be further substituted as will be apparent to those having skill in the organic and medicinal chemistry arts in conjunction with the disclosure herein.

"Arylcarbonylamino" refers herein to —N(R$^b$)C(═O)-aryl, wherein R$^b$ is as defined above.

"Heterocyclylcarbonylamino" refers herein to —N(R$^b$)C(═O)-heterocylyl wherein R$^b$ is as defined above.

"Alkoxycarbonylamino" refers herein to —N(R$^b$)C(═O)O-alkyl wherein R$^b$ is as defined above.

"Aryloxycarbonylamino" refers herein to —N(R$^b$)C(═O)O-aryl wherein R$^b$ is as defined above.

"Heterocyclyloxycarbonylamino" refers herein to —N(R$^b$)C(═O)O-heterocyclyl wherein R$^b$ is as defined above.

"Sulfonyl" refers herein to the group —SO$_2$—.

"Alkylsulfonylamino" refers herein to —NR$^b$S(═O)$_2$-alkyl wherein R$^b$ is as defined above.

"Arylsulfonylamino" refers herein to —NR$^b$S(═O)$_2$-aryl wherein R$^b$ is as defined above.

"Heterocyclylsulfonyllamino" refers herein to —NR$^b$S(═O)$_2$-heterocyclyl wherein R$^b$ is as defined above.

"Aminosulfonyl" refers herein to —S(═O)$_2$NR$^b$R$^b$ wherein each R$^b$ independently selected from H, alkyl, aryl, heteroaryl or heterocyclyl.

"Alkylsulfonyl" refers herein to —S(═O)$_2$-alkyl. Alkylsulfonyl groups employed in compounds of the present invention are typically alkylsulfonyl groups having from 1 to 6 carbon atoms in its backbone structure. Thus, typical alkylsulfonyl groups employed in compounds of the present invention include, for example, methylsulfonyl (i.e., where alkyl is methyl), ethylsulfonyl (i.e., where alkyl is ethyl), propylsulfonyl (i.e., where alkyl is propyl), and the like.

"Arylsulfonyl" refers herein to —S(═O)$_2$-aryl.

"Heterocyclylsulfonyl" refers herein to —S(═O)$_2$-heterocyclyl.

The term "sulfonamido" refers herein to —SO$_2$NH$_2$.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

Included in the invention is the free form of compounds of formulae I-IV, as well as the pharmaceutically acceptable salts, stereoisomers, and prodrugs thereof.

As used herein, the term "pharmaceutically acceptable salts" refers to the nontoxic acid or alkaline earth metal salts of the compounds of formulae I-IV. These salts can be prepared in situ during the final isolation and purification of the compounds of formulae I-IV, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2 hydroxyethanesulfonate, lactate, maleate, methanesulfonate, nicotinate, 2 napthalenesulfonate, oxalate, pamoate, pectinate, persulfate, 3 phenylproionate, picrate, pivalate, propionate, succinate, sulfate, tartrate, thiocyanate, p toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formulae I-IV, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters which may hydrolyze in vivo and include those that break down in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "anticancer agent" refers to agents synthesized or modified in the laboratory which have anticancer activity. An "anticancer" agent in this context will inhibit the growth of tumor. The term "inhibiting the growth" indicates that the rate of increase in the size and/or weight of tumor are reduced. Thus, the term includes situations in which the tumor size and/or weight increases but at a reduced rate, as well as situations where the growth of the tumor is stopped. If an enzyme activity assay is used to screen for inhibitors, one can make modifications in uptake/efflux, solubility, half life, etc. to compounds in order to correlate enzyme inhibition with growth inhibition. This term is more thoroughly described in the next section.

The subject invention also includes isotopically-labeled compounds, which are structurally identical to those disclosed above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

B. Uses, Dosage and Administration

The present invention provides novel compounds, pharmaceutical compositions including the compounds, methods of inhibiting KSP, and methods of treating KSP-mediated diseases including cellular proliferative disorders, such as cancer.

In one aspect, the present invention provides methods of treating human or animal subjects suffering from a cellular proliferative disease. The term "cellular proliferative disorder" or "cell proliferative disorder" refers to diseases including, for example, cancer, tumor, hyperplasia, restenosis, cardiac hypertrophy, immune disorder and inflammation. The present invention provides methods of treating a human or animal subject in need of such treatment, comprising administering to the subject a therapeutically effective amount of a compound of formulae I-IV, either alone or in combination with other anticancer agents.

The compounds of the invention are useful in vitro or in vivo in inhibiting the growth of cancer cells. The term "cancer" refers to cancer diseases including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

Cancer also includes tumors or neoplasms selected from the group consisting of carcinomas, adenocarcinomas and sarcomas.

Additionally, the type of cancer can be selected from the group consisting of growth of solid tumors/malignancies, myxoid and round cell carcinoma, locally advanced tumors, human soft tissue carcinoma, cancer metastases, squamous cell carcinoma, esophageal squamous cell carcinoma, oral carcinoma, cutaneous T cell lymphoma, Hodgkin's lymphoma, non-Hodgkin's lymphoma, cancer of the adrenal cortex, ACTH-producing tumors, nonsmall cell cancers, breast cancer, gastrointestinal cancers, urological cancers, malignancies of the female genital tract, malignancies of the male genital tract, kidney cancer, brain cancer, bone cancers, skin cancers, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In still yet another preferred embodiment, the cell proliferative disorder is selected from the group consisting of angiogenesis-mediated diseases, benign tumors, acoustic neuromas, neurofibromas, pyogenic granulomas, biliary tract cancer, choriocarcinoma, esophageal cancer, gastric cancer, intraepithelial neoplasms, lung cancer, neuroblastomas, chronic myelogenous leukemia, acute myelogenous leukemia, and multiple myeloma.

The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey, 1991, incorporated herein by reference.

In one aspect, the present invention provides pharmaceutical compositions comprising at least one compound of formulae I-IV together with a pharmaceutically acceptable carrier suitable for administration to a human or animal subject, either alone or together with other anticancer agents.

Effective amounts of the compounds of the invention generally include any amount sufficient to inhibit KSP activity by the assay described herein, by other KSP activity assays known to those having ordinary skill in the art, or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

In another embodiment, the present invention provides methods for treating a cellular proliferative disease in a human or animal subject in need of such treatment comprising, administering to said subject an amount of a compound of formulae I-IV effective to reduce or prevent cellular proliferation or tumor growth in the subject.

In other aspects, the invention provides methods for using the compounds described herein. For example, the compounds described herein can be used in the treatment of cancer. The compounds described herein can also be used in the manufacture of a medicament for the treatment of cancer.

In another embodiment, the present invention provides methods for treating a cellular proliferative disease in a human or animal subject in need of such treatment comprising administering to said subject an amount of a compound of formulae I-IV effective to reduce or prevent cellular proliferation in the subject in combination with at least one additional agent for the treatment of cancer.

A number of suitable anticancer agents to be used as combination therapeutics are contemplated for use in the compositions and methods of the present invention. Suitable anticancer agents to be used in combination with the compounds of the invention include agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons [e.g. IFN-a] and interleukins [e.g. IL-2]); adoptive immunotherapy agents; hematopoietic growth factors; agents that induce tumor cell differentiation (e.g. all-trans-retinoic acid); gene therapy reagents; antisense therapy reagents and nucleotides; tumor vaccines; inhibitors of angiogenesis, and the like. Numerous other examples of chemotherapeutic compounds and anticancer therapies suitable for coadministration with the disclosed compounds of formulae I-IV are known to those skilled in the art.

In preferred embodiments, anticancer agents to be used in combination with compounds of the present invention comprise agents that induce or stimulate apoptosis. Agents that induce apoptosis include, but are not limited to, radiation; kinase inhibitors (e.g., Epidermal Growth Factor Receptor [EGFR] kinase inhibitor, Vascular Growth Factor Receptor [VGFR] kinase inhibitor, Fibroblast Growth Factor Receptor [FGFR] kinase inhibitor, Platelet-derived Growth Factor Receptor [PGFR] I kinase inhibitor, and Bcr-Abl kinase inhibitors such as STI-571, Gleevec, and Glivec]); antisense molecules; antibodies [e.g., Herceptin and Rituxan]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib, meloxicam, NS-398, and non-steroidal anti-inflammatory drugs (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP 16, cisplatinum, 5-FU, Doxrubicin, TAXOTERE or TAXOL]; cellular signaling molecules; ceramides and cytokines; and staurosprine; and the like.

The present invention provides compounds that are inhibitors of KSP. The inhibitors are useful in pharmaceutical compositions for human or veterinary use where inhibition of KSP is indicated, e.g., in the treatment of cellular proliferative diseases such as tumor and/or cancerous cell growth mediated by KSP. In particular, the compounds are useful in the treatment of human or animal (e.g., murine) cancer. The compounds of the invention are useful in treating cancers, such as, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

In another embodiment, the invention provides methods of treating a KSP mediated disorder in a human or animal subject comprising administering to a human or animal subject in need of such treatment a therapeutically effective amount of a compound of formulae I-IV. The term "KSP mediated disorder" refers to a disorder that can be beneficially treated by the inhibition of KSP. As used throughout, this disorder is referred to as a disorder mediated, at least in part, by KSP. In one method, an effective amount of a compound of formulae I-IV is administered to a patient (e.g., a human or animal subject) in need thereof to mediate (or modulate) KSP activity.

In some embodiments of the method of inhibiting KSP using a compound of formulae I-IV, the $IC_{50}$ value of the compound is less than or equal to 1 mM with respect to KSP. In other such embodiments, the $IC_{50}$ value is less than or equal to 100 µM, is less than or equal to 25 µM, is less than or equal to 10 µM, is less than or equal to 1 µM, is less than or equal to 0.1 µM, is less than or equal to 0.050 µM, or is less than or equal to 0.010 µM.

C. Pharmaceutical Compositions and/or Formulations

Pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations may also be prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol and inhalable dry powder formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of a aerosol particles having with a mass medium average diameter predominantly between 1 to 5 μM. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 μM. Predominantly in this application means that at least 70% but preferably more than 90% of all generated aerosol particles are 1 to 5 μM range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb® and AeroDose® vibrating porous plate nebulizers (AeroGen, Inc., Sunnyvale, Calif.), Sidestream® nebulizers (Medic-Aid Ltd., West Sussex, England), Pari LC® and Pari LC Star® jet nebulizers (Pari Respiratory Equipment, Inc., Richmond, Va.), and Aerosonic® (DeVilbiss Medizinische Produkte (Deutschland) GmbH, Heiden, Germany) and UltraAire® (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, cancers are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat cancer, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

Methods of formulation are well known in the art and are disclosed, for example, in Remington: The Science and Practice of Pharmacy, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

A "kit" as used in the instant application includes a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid, where the written memory aid is of the type containing information and/or instructions for the physician, pharmacist or other health care provider, or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc. . . . "Second Week, Monday, Tuesday, . . . " etc. Other variations of memory aids will be readily apparent. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablets or capsules.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter, which indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

The kits of the present invention may also include, in addition to KSP inhibitors, one or more additional pharmaceutically active compounds. Preferably, the additional compound is another KSP inhibitor or another compound useful in treating cancer. The additional compounds may be administered in the same dosage form as the KSP inhibitor or in different dosage forms. Likewise, the additional compounds can be administered at the same time as the KSP inhibitor or at different times.

Compositions of the present compounds may also be used in combination with other known anticancer agents of similar spectrum to synergistically enhance treatment of cancer. The treatment can involve administering a composition having both active agents or administration of the inventive compounds followed by or preceded by administration of an additional active anticancer agent.

While the compounds of the invention can be administered as the sole active pharmaceutical agent, they can also be used in combination with one or more other agents used in the treatment of cancer. Representative agents useful in combination with the compounds of the invention for the treatment of cancer include, for example, irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab, topoisomerase I inhibitors, as well as other cancer chemotherapeutic agents.

The above compounds to be employed in combination with the compounds of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan, et al, J. Biol. Chem. 276:40888, 2001). As reported by Donovan et al., inhibition of MAPK signaling through treatment with MEK inhibitor changed the phosphorylation status of p27 in hormone refactory breast cancer cell lines and in so doing restored hormone sensitivity. Accordingly, in one aspect, the compounds of formulae I-IV may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-AB1 tyrosine kinase. Some afflicted patients are responsive to gleevec, a small molecule tyrosine kinase inhibitor, as a result of inhibition of Ab1 kinase activity. However, many patients with advanced stage disease respond to gleevec initially, but then relapse later due to resistance-conferring mutations in the Ab1 kinase domain. In vitro studies have demonstrated that BCR-Av1 employs the Raf kinase pathway to elicit its effects. In addition, inhibiting more than one kinase in the same pathway provides additional protection against resistance-conferring mutations. Accordingly, in another aspect of the invention, the compounds of formulae I-IV are used in combination with at least one additional agent, such as gleevec, in the treatment of hematological cancers, such as chronic myelogenous leukemia (CML), to reverse or prevent resistance to the at least one additional agent.

D. Methods of Making Compounds of the Invention

The present invention also provides methods of manufacture of compounds of formulae I-IV as described herein.

The present invention also relates to the processes for preparing the compounds of the invention and to the synthetic intermediates useful in such processes, as described in detail below. The syntheses of representative compounds of the invention are described in Examples 1-3. One skilled in the art will appreciate that the compounds of the invention can be prepared by standard synthetic organic chemical methods.

In some embodiments, the invention provides for methods of making compounds of formulae I-IV as described in Examples 1-3. It is further contemplated that the present invention covers the intermediates as well as their corresponding methods of synthesis as described in Examples 1-3.

A representative assay for determining KSP inhibitory activity is described in Example 4.

The present invention will be understood more readily by reference to the following examples, which are provided by way of illustration and are not intended to be limiting of the present invention.

EXAMPLES

Referring to the examples that follow, compounds of the present invention were synthesized using the methods described herein, or other methods, which are well known in the art.

The compounds and/or intermediates were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses were reported as those of the protonated parent ions.

GCMS analysis is performed on a Hewlett Packard instrument (HP6890 Series gas chromatograph with a Mass Selective Detector 5973; injector volume: 1 µL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.)

Melting points are determined on a Laboratory Devices MeI-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

Unless otherwise stated all temperatures are in degrees Celsius. Also, in these examples and elsewhere, abbreviations have the following meanings:

| | |
|---|---|
| AcOH = | Acetic acid |
| aq = | Aqueous |
| ATP = | Adenosine triphosphate |
| 9-BBN = | 9-Borabicyclo[3.3.1]nonane |
| Boc = | tert-butoxycarbonyl |
| Celite = | Filter agent |
| DAP or Dap = | Diaminopropionate |
| DCM = | Dichloromethane |
| DEAD = | Diethyl azodicarboxylate |
| DIEA = | Diisopropylethylamine |
| DMAP = | 4-Dimethylaminopyridine |
| DME = | 1,2-dimethoxyethane |
| DMF = | N,N-Dimethylformamide |
| DMSO = | Dimethyl sulfoxide |
| DPPA = | Diphenyl phosphoryl azide |
| $Et_3N$ = | Triethylamine |
| EDC = | N-(3-Dimethylaminopropyl)-N'-ethylcarbodiimide |
| EDCI = | 1-(3-dimethylaminopropyl)3-ethylcarbodiimide |
| EtOAc = | Ethyl acetate |
| EtOH = | Ethanol |
| Fmoc = | 9-fluorenylmethoxycarbonyl |
| Gly-OH = | glycine |
| HATU = | O-(7-azabenzotriaazol-1-yl)-N,N,N'N' = tetramethyluronium hexafluorophophate |
| HBTU = | 2-(1H-benzotriazol-1-yl)-1,1,3,3-tetramethyluronium hexafluorophosphate |
| Hex = | hexane |
| HOBt = | butyl alcohol |
| HOBT = | 1-Hydroxybenzotriazole |
| HPLC = | High Pressure Liquid Chromatography |
| NIS = | N-iodosuccinimide |
| $IC_{50}$ value = | The concentration of an inhibitor that causes a 50% reduction in a measured activity. |
| iPrOH = | Isopropanol |
| LC/MS = | Liquid Chromatography/Mass Spectrometry |
| LRMS = | Low Resolution Mass Spectrometry |

-continued

| | |
|---|---|
| MeOH = | Methanol |
| NaOMe = | sodium methoxide |
| nm = | Nanometer |
| NMP = | N-Methylpyrrolidone |
| PPA = | Polyphosphoric acid |
| PPh$_3$ = | triphenyl phosphine |
| PTFE = | Polytetrafluoroethylene |
| RP-HPLC = | Reversed-phase high-pressure liquid chromatography |
| RT = | Room temperature |
| sat = | Saturated |
| TEA = | Triethylamine |
| TFA = | Trifluoroacetic acid |
| THF = | Tetrahydrofuran |
| Thr = | Threonine |
| TLC = | Thin Layer Chromatography |
| Trt-Br = | Tert-butyl bromide |

Nomenclature for the Example compounds was provided using ACD Name version 5.07 software (Nov. 14, 2001) available from Advanced Chemistry Development, Inc. Some of the compounds and starting materials were named using standard IUPAC nomenclature.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

It is understood that the invention is not limited to the embodiments set forth herein for illustration, but embraces all such forms thereof as come within the scope of the above disclosure.

Example 1

N-(3-Aminopropyl)-N-[1-(3-benzyl-4-oxo-6,7,8,9-tetrahydro-4H-pyrido[1,2-a]pyrimidin-2-yl)-2-methylpropyl]-4-methylbenzamide

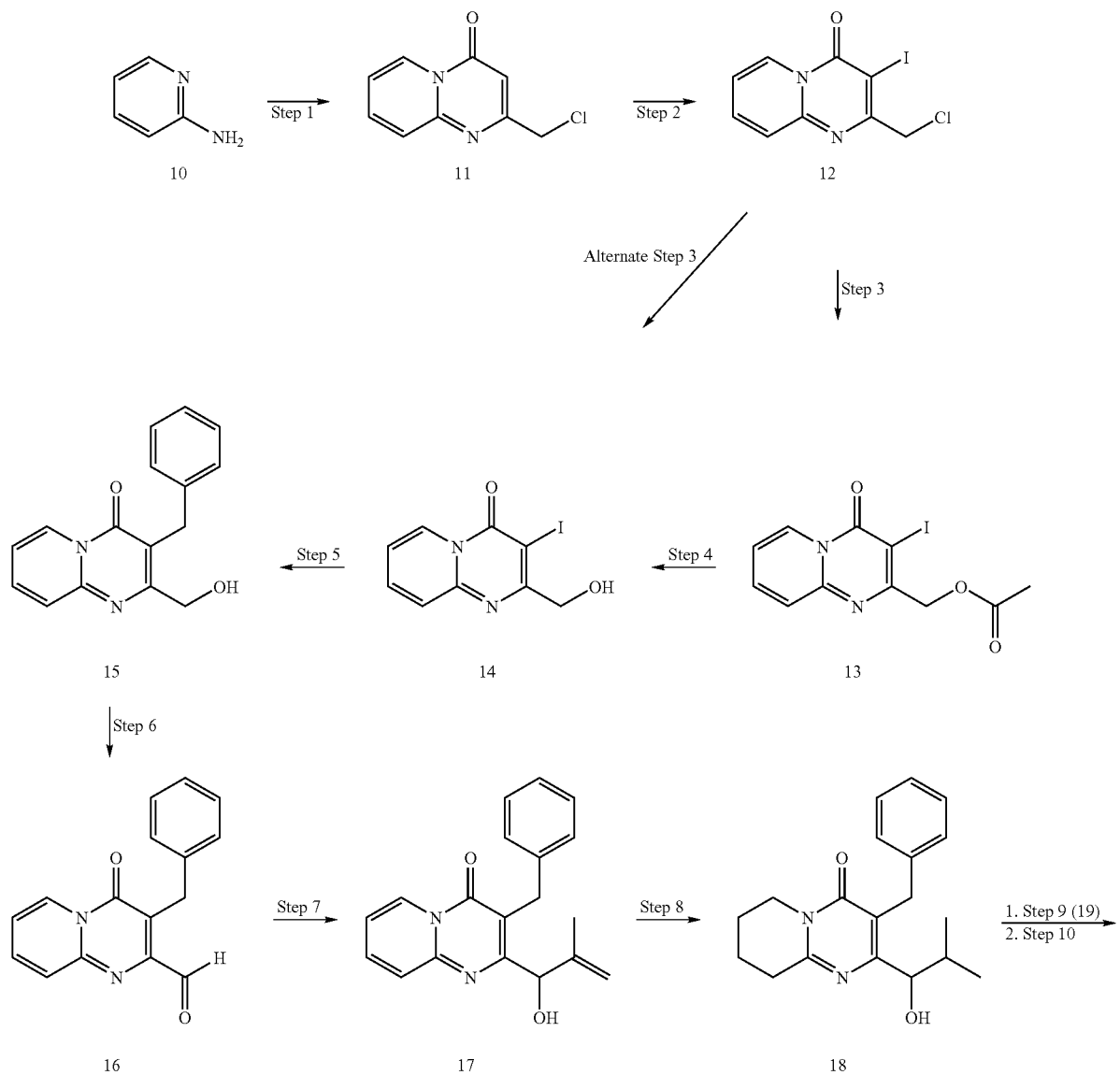

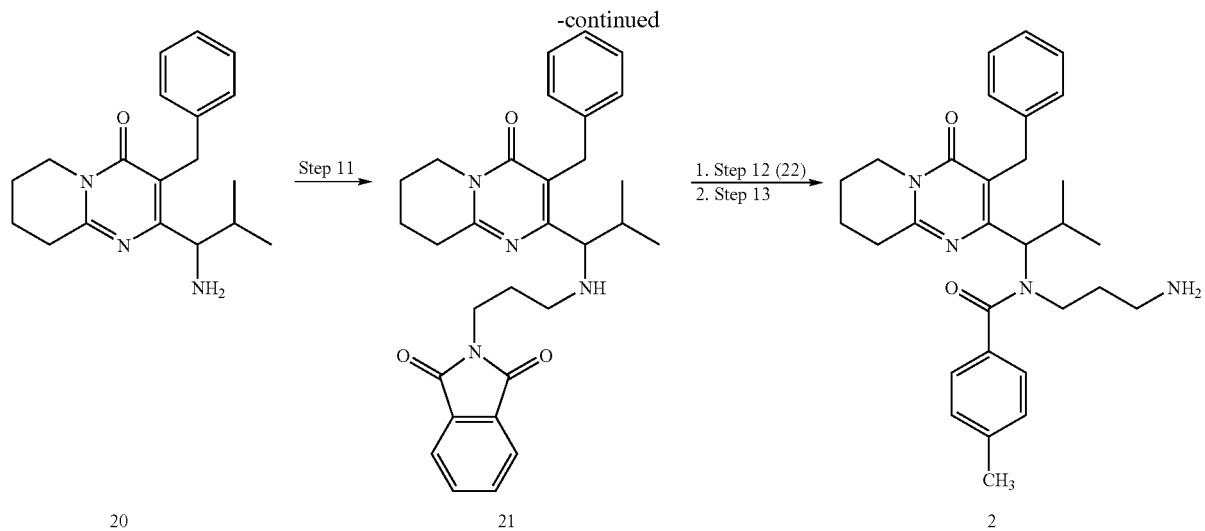

Step 1.
2-(Chloromethyl)-4H-pyrido[1,2-a]pyrimidin-4-one

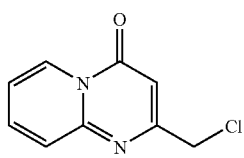

11

15 g (159.4 mmol) of 2-aminopyridine (10) was combined with approximately 80 g of polyphosphoric acid and heated to 120° C. to allow stirring. To the resulting solution was slowly added 30.5 mL (223.2 mmol) of ethyl-4-chloroacetoacetate and stirred at 120° C. under nitrogen for two hours. The hot reaction mixture was then poured over 1500 mL of ice water and stirred vigorously. The aqueous layer was separated and extracted with methylene chloride (6×, approximately 6 L). The combined organic layers were washed with saturated NaHCO$_3$ and brine and dried over MgSO$_4$ and activated carbon. The solvent was removed in vacuo yielding 30.7 g (157.7 mmol, 99%) of 2-(chloromethyl)-4H-pyrido[1,2-a]pyrimidin-4-one (11) as a white solid.

Step 2. 2-(Chloromethyl)-3-iodo-4H-pyrido[1,2-a]pyrimidin-4-one

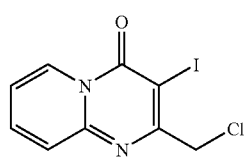

12

A mixture of 21.9 g (112.5 mmol) of the product from Step 1 (11) and 38.9 g (168.8 mmol) of N-iodosuccinimide in 660 mL of acetonitrile was stirred at 80° C. under nitrogen for 16 hours. The reaction mixture was then allowed to cool to ambient temperature and the acetonitrile was removed in vacuo. The resulting solid was washed with water, saturated Na$_2$O$_3$S$_2$, saturated NaHCO$_3$, and brine, and then filtered. Drying under reduced pressure at 40° C. overnight yielded 29.8 g (92.9 mmol, 83%) of 2-(chloromethyl)-3-iodo-4H-pyrido[1,2-a]pyrimidin-4-one (12) as a light brown solid.

Step 3. (3-Iodo-4-oxo-4H-pyrido[1,2-a]pyrimidin-2-yl)methyl acetate

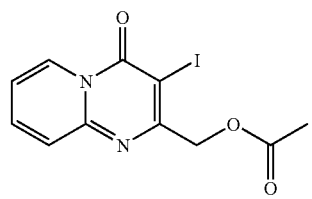

13

A mixture of 20.0 g (62.4 mmol) of the product from Step 2 (12) and 9.2 g (93.6 mmol) of potassium acetate in 200 mL DMF was stirred at 40° C. under nitrogen for three hours. The reaction mixture was allowed to cool to ambient temperature and the addition of excess water to the reaction solution caused the product to precipitate out of solution. The product was filtered, washed with water (3×), and drying under reduced pressure at 40° C. overnight yielded 19.4 g (56.4 mmol, 90%) of (3-iodo-4-oxo-4H-pyrido[1,2-a]pyrimidin-2-yl)methyl acetate (13) as a white solid.

Alternatively, the product from step 2 (12) can undergo hydrolysis to provide the corresponding alcohol (14).

Step 4. 2-(Hydroxymethyl)-3-iodo-4H-pyrido[1,2-a]pyrimidin-4-one

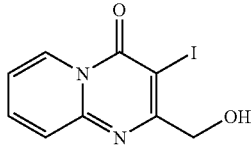

14

A mixture of 16.5 g (48.0 mmol) of the product from Step 3 (13) and 13.3 g (96.0 mmol) of potassium carbonate in 300 mL of methanol was stirred at ambient temperature for 3 hours. Excess water was added to the reaction mixture and the mixture was extracted using ethyl acetate (3×). The organic layers were combined, dried over $MgSO_4$ and activated carbon, and the solvent was removed in vacuo yielding 12 g (39.7 mmol, 83%) of 2-(hydroxymethyl)-3-iodo-4H-pyrido[1,2-a]pyrimidin-4-one (14) as a white solid.

Step 5. 3-Benzyl-2-(hydroxymethyl)-4H-pyrido[1,2-a]pyrimidin-4-one

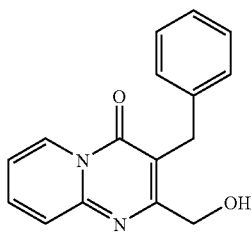

15

A mixture of 4.0 g (13.24 mmol) of the product from Step 4 (14), 1.0 g (1.32 mmol) of dichloro[1,1'-bis(diphenylphosphino)ferrocene] palladium(II) dichloromethane adduct, and 8.4 g (39.72 mmol) of $K_3PO_4$ in 30 mL of DMF was heated to 80° C. To the resulting solution was added dropwise 40 mL (19.9 mmol) of B-Benzyl-9-BBN and stirred at 80° C. under nitrogen for 12 hours. The reaction was then cooled to 0° C. and excess 1N NaOH was added to the reaction mixture. Excess 30% $H_2O_2$ was then added to the mixture at 0° C. resulting in significant gas evolution. Stirring continued for at least one additional hour or until gas ceased to evolve. The mixture was extracted with ethyl acetate (3×) and washed with saturated $Na_2O_3S_2$ and brine. The organic layers were combined, dried over $MgSO_4$ and activated carbon, and the solvent was removed in vacuo. The resulting material was subjected to flash chromatography on a 10 cm column. Elution with a gradient of 100% hexanes, 20% ethyl acetate in hexanes, 33% ethyl acetate in hexanes, 43% ethyl acetate in hexanes, 50% ethyl acetate in hexanes, 57% ethyl acetate in hexanes, 67% ethyl acetate in hexanes, and 100% ethyl acetate yielded 3.2 g (12.0 mmol, 91%) of 3-benzyl-2-(hydroxymethyl)-4H-pyrido[1,2-a]pyrimidin-4-one (15) as a pale yellow solid.

Step 6. 3-Benzyl-4-oxo-4H-pyrido[1,2-a]pyrimidine-2-carbaldehyde

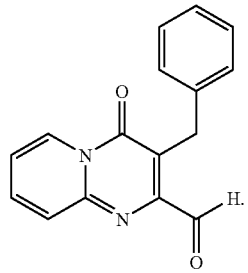

16

26.5 mL (53.0 mmol) of oxalyl chloride in 40 mL dichloromethane was cooled to −78° C. To the resulting solution was added a solution of 7.52 mL (105.9 mmol) of DMSO in 24 mL dichloromethane and stirred at −78° C. for one hour. Then was added a solution of 4.7 g (17.65 mmol) of the product from Step 5 (15) in 60 mL dichloromethane and the resulting mixture was stirred at −78° C. for one hour. Then was added 24.6 mL (176.5 mmol) of triethylamine and stirred at −78° C. for one hour. The mixture was then allowed to warm to 0° C. and stirred for another hour. Finally, the mixture was allowed to warm to ambient temperature over the course of one hour. Excess water was added to the reaction mixture and the mixture was extracted (3×) using dichloromethane. The combined organic layers were dried over $MgSO_4$ and activated carbon and the solvent was removed in vacuo. The resulting material was subjected to flash chromatography on a 10 cm column. Elution with a gradient of 100% hexanes, 20% ethyl acetate in hexanes, 33% ethyl acetate in hexanes, 43% ethyl acetate in hexanes, and 50% ethyl acetate in hexanes yielded 3.1 g (11.7 mmol, 67%) of 3-benzyl-4-oxo-4H-pyrido[1,2-a]pyrimidine-2-carbaldehyde (16) as a yellow solid.

Step 7. 3-Benzyl-2-(1-hydroxy-2-methylprop-2-enyl)-4H-pyrido [1,2-a]pyrimidin-4-one

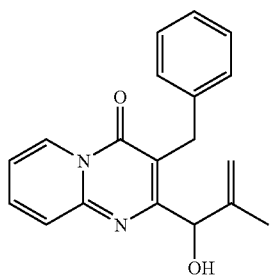

17

A mixture of 500 mg (1.9 mmol) of the product from Step 6 (16) in 15 ml THF was cooled to −78° C. To the resulting solution was added dropwise 7.6 ml (3.8 mmol) of isopropenylmagnesium bromide and stirred at −78° C. for 2 hours. The reaction was quenched with saturated $NH_4Cl$ and extracted with ethyl acetate (2×). The combined organic layers were dried over $MgSO_4$ and the solvent was removed in vacuo yielding 613 mg (2.0 mmol, 106%) of 3-benzyl-2-(1-hydroxy-2-methylprop-2-enyl)-4H-pyrido [1,2-a]pyrimidin-4-one (17) as a pale yellow solid. This was purified by flash chromatography.

Step 8. 3-Benzyl-2-(1-hydroxy-2-methylpropyl)-6,7,8,9-tetrahydro-4H-pyrido [1,2-a]pyrimidin-4-one

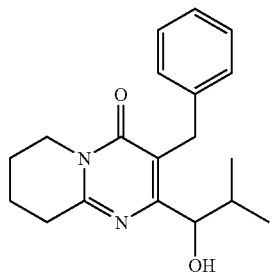

18

After the product from Step 7 (17) was purified, 100 mg (0.33 mmol) and 85 mg of Palladium on activated carbon was stirred in 5 ml of ethanol. The flask was equipped with a balloon containing hydrogen gas and the reaction mixture was stirred at ambient temperature overnight. The reaction mixture was then filtered through a PTFE filter and washed with ethyl acetate. The resulting product was concentrated yielding 90 mg (0.29 mmol, 88%) of 3-benzyl-2-(1-hydroxy-2-methylpropyl)-6,7,8,9-tetrahydro-4H-pyrido[1,2-a]pyrimidin-4-one (18) as a clear oil.

Step 9. 2-[1-(3-Benzyl-4-oxo-6,7,8,9-tetrahydro-4H-pyrido[1,2-a]pyrimidin-2-yl)-2-methylpropyl]-1H-isoindole-1,3(2H)-dione

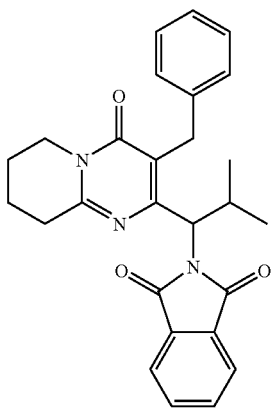

19

A previous batch of the product from Step 8 (18) was combined with the above and 150 mg (0.48 mmol) of this crude material was dissolved in 3 ml of dry tetrahydrofuran then cooled to 0° C. Phthalimide 212 mg (1.4 mmol) was added to the cold solution followed by triphenylphosphine 189 mg (0.72 mmol) then DIAD 140 μl (0.72 mmol). The reaction mixture was stirred under nitrogen and allowed to warm to room temperature overnight. The solvent was evaporated and the solid redissolved in ethyl acetate then washed with saturated NaHCO₃ and brine. The organic layer was then dried over MgSO₄ and the solvent was removed in vacuo resulting in 700 mg of crude material that was purified by flash chromatography to give 95 mg (0.22 mmol, 44%) of 2-[1-(3-benzyl-4-oxo-6,7,8,9-tetrahydro-4H-pyrido[1,2-a]pyrimidin-2-yl)-2-methylpropyl]-1H-isoindole-1,3(2H)-dione (19) as a white solid.

Step 10. 2-(1-Amino-2-methylpropyl)-3-benzyl-6,7,8,9-tetrahydro-4H-pyrido[1,2-a]pyrimidin-4-one

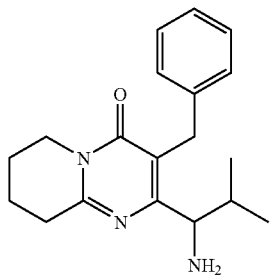

20

The product from Step 9 (19), 95 mg (0.22 mmol) was dissolved in 3 ml of dry ethanol then 50 μl (1.6 mmol) of hydrazine was added and the reaction was left to stir at room temperature for 1 h then heated to 40° C. for 2.5 h. The precipitate was removed by filtration and washed with ethyl acetate and the solvent evaporated off resulting in 75 mg of crude 2-(1-amino-2-methylpropyl)-3-benzyl-6,7,8,9-tetrahydro-4H-pyrido[1,2-a]pyrimidin-4-one (20). This was purified on a silica column yielding 42 mg (0.13 mmol 63%) as a clear oil.

Step 11. 2-(3-{[1-(3-Benzyl-4-oxo-6,7,8,9-tetrahydro-4H-pyrido[1,2-a]pyrimidin-2-yl)-2-methylpropyl]amino}propyl)-1H-isoindole-1,3(2H)-dione

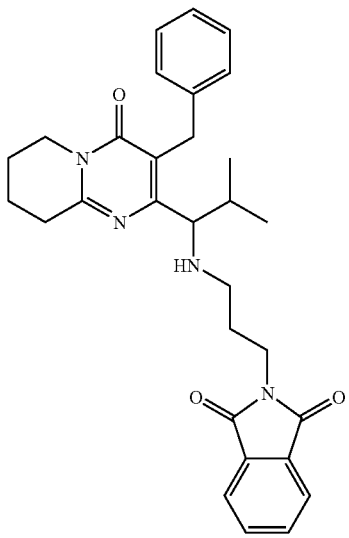

21

The product from Step 10 (20), 42 mg (0.13 mmol) was dissolved in anhydrous $CH_2Cl_2$ followed by the addition of phthalimide protected 3-aminopropionaldehyde 33 mg (0.16 mmol) and 37 mg (0.18 mmol) of sodium acetoxyborohydride and finally 10 μl (0.18 mmol) of acetic acid. The reaction was left stirring at room temperature for 2.5 h. The solvent was evaporated and the product redissolved in ethyl acetate and washed with saturated $NaHCO_3$ and brine. The organic layer was dried over $MgSO_4$, filtered and concentrated and dried under high vacuum resulting in 63 mg (0.13 mmol, 94%) of 2-(3-{[1-(3-benzyl-4-oxo-a]pyrimidin-2-yl)-2-methylpropyl]amino}propyl)-1H-isoindole-1,3(2H)-dione (21) as a white solid.

Step 12. N-[1-(3-Benzyl-4-oxo-6,7,8,9-tetrahydro-4H-pyrido[1,2-a]pyrimidin-2-yl)-2-methylpropyl]-N-[3-(1,3-dioxo-1,3-dihydro-2H-isoindol-2-yl)propyl]-4-methylbenzamide

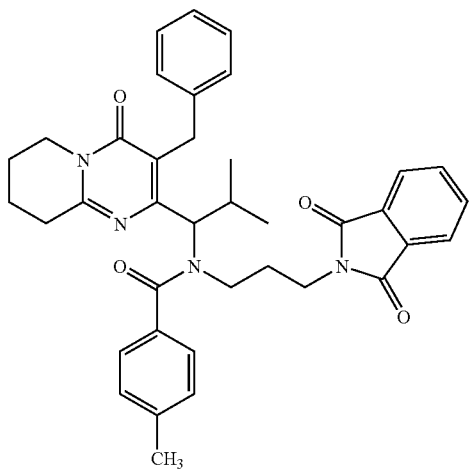

22

The product from Step 11(21), 63 mg (0.13 mmol) was dissolved in $CH_2Cl_2$ followed by the addition of 33 μl (0.25 mmol) 4-methyl benzoyl chloride and 53 μl (0.38 mmol) triethylamine. The reaction was left to stir at room temperature for 2 h. The ethyl acetate layer was washed with saturated $NaHCO_3$ and brine. The organic layer was dried over $MgSO_4$, filtered and concentrated. The product was purified by flash chromatography resulting in 50 mg (0.08 mmol, 64%) of N-[1-(3-benzyl-4-oxo-6,7,8,9-tetrahydro-4H-pyrido[1,2-a]pyrimidin-2-yl)-2-methylpropyl]-N-[3-(1,3-dioxo-1,3-dihydro-2H-isoindol-2-yl)propyl]-4-methylbenzamide (22) as a white solid.

Step 13. N-(3-Aminopropyl)-N-[1-(3-benzyl-4-oxo-6,7,8,9-tetrahydro-4H-pyrido[1,2-a]pyrimidin-2-yl)-2-methylpropyl]-4-methylbenzamide

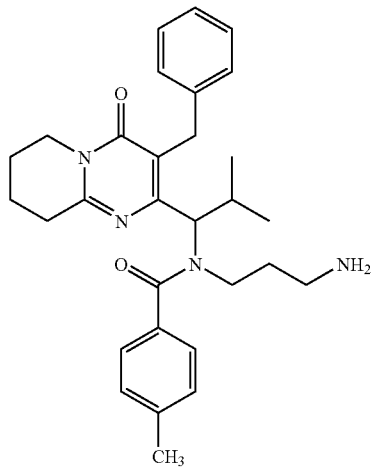

2

The product from Step 12 (22), 50 mg (0.08 mmol) was dissolved in 1 ml of anhydrous ethanol. Hydrazine 18 μl (0.57 mmol) was added and the reaction stirred at room temperature for 2 h. The precipitate was filtered through a PTFE filter and washed with ethyl acetate. The solvent was evaporated and the crude material was purified by reverse phase HPLC resulting to 11 mg (0.023 mmol) of N-(3-aminopropyl)-N-[1-(3-benzyl-4-oxo-6,7,8,9-tetrahydro-4H-pyrido[1,2-a]pyrimidin-2-yl)-2-methylpropyl]-4-methylbenzamide (2) as the TFA salt.

Example 2

N-(3-Aminopropyl)-N-[1-(3-benzyl-4-oxo-6,7,8,9-tetrahydro-4H-pyrido[1,2-a]pyrimidin-2-yl)propyl]-4-bromobenzamide -continued

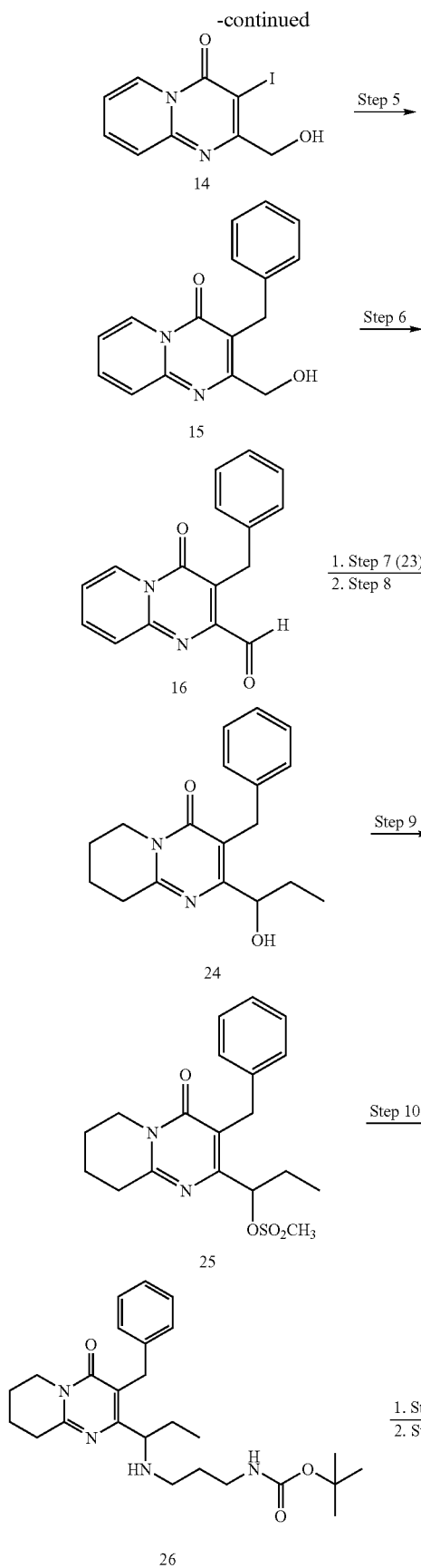

-continued

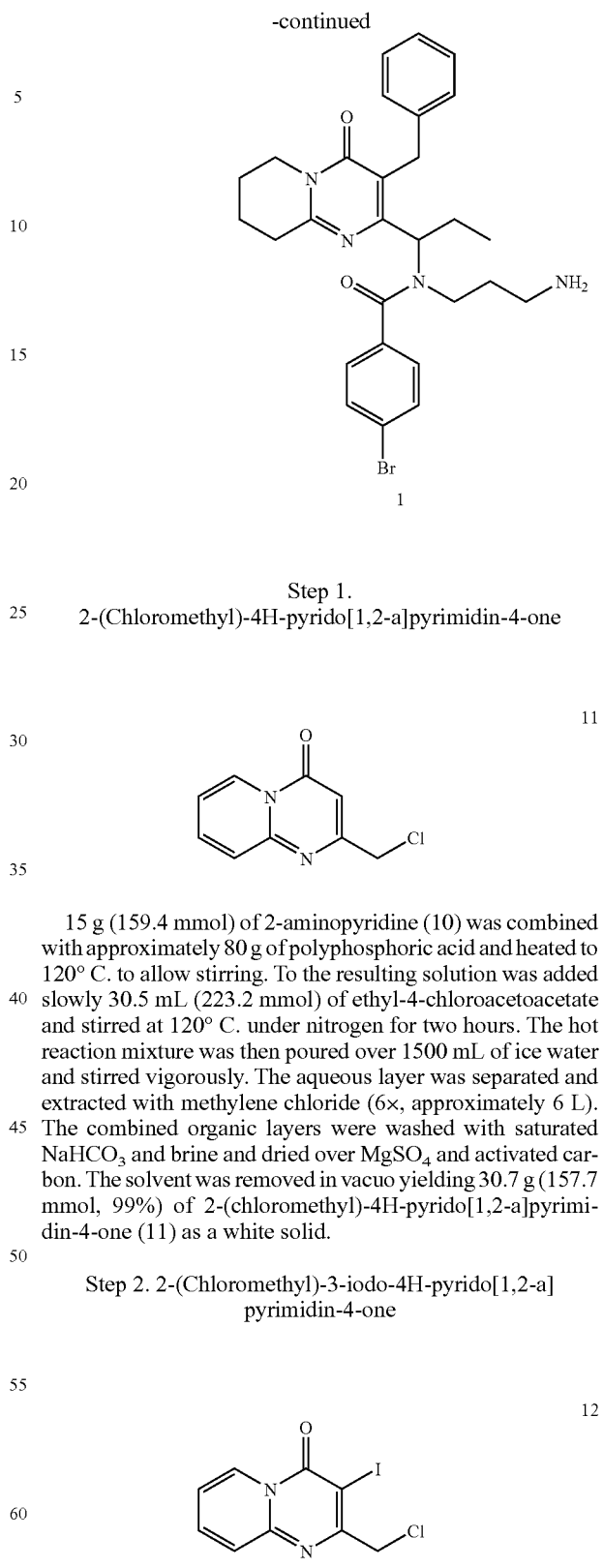

Step 1.
2-(Chloromethyl)-4H-pyrido[1,2-a]pyrimidin-4-one 15 g (159.4 mmol) of 2-aminopyridine (10) was combined with approximately 80 g of polyphosphoric acid and heated to 120° C. to allow stirring. To the resulting solution was added slowly 30.5 mL (223.2 mmol) of ethyl-4-chloroacetoacetate and stirred at 120° C. under nitrogen for two hours. The hot reaction mixture was then poured over 1500 mL of ice water and stirred vigorously. The aqueous layer was separated and extracted with methylene chloride (6×, approximately 6 L). The combined organic layers were washed with saturated NaHCO₃ and brine and dried over MgSO₄ and activated carbon. The solvent was removed in vacuo yielding 30.7 g (157.7 mmol, 99%) of 2-(chloromethyl)-4H-pyrido[1,2-a]pyrimidin-4-one (11) as a white solid.

Step 2. 2-(Chloromethyl)-3-iodo-4H-pyrido[1,2-a]pyrimidin-4-one

A mixture of 21.9 g (112.5 mmol) of the product from Step 1 (11) and 38.9 g (168.8 mmol) of N-iodosuccinimide in 660 mL of acetonitrile was stirred at 80° C. under nitrogen for 16 hours. The reaction mixture was then allowed to cool to ambient temperature and the acetonitrile was removed in vacuo. The resulting solid was washed with water, saturated Na₂O₃S₂, saturated NaHCO₃, brine, and filtered. Drying under reduced pressure at 40° C. overnight yielded 29.8 g (92.9 mmol, 83%) of 2-(chloromethyl)-3-iodo-4H-pyrido[1, 2-a]pyrimidin-4-one (12) as a light brown solid.

Step 3. (3-Iodo-4-oxo-4H-pyrido[1,2-a]pyrimidin-2-yl)methyl acetate

13

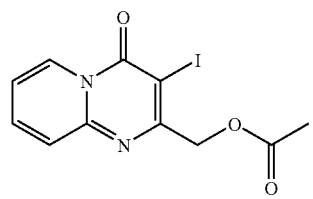

A mixture of 20.0 g (62.4 mmol) of the product from Step 2 (12) and 9.2 g (93.6 mmol) of potassium acetate in 200 mL DMF was stirred at 40° C. under nitrogen for three hours. The reaction mixture was allowed to cool to ambient temperature and the addition of excess water to the reaction solution caused the product to precipitate out of solution. The product was filtered, washed with water (3×), and drying under reduced pressure at 40° C. overnight yielded 19.4 g (56.4 mmol, 90%) of (3-iodo-4-oxo-4H-pyrido[1,2-a]pyrimidin-2-yl)methyl acetate (13) as a white solid.

Step 4. 2-(Hydroxymethyl)-3-iodo-4H-pyrido[1,2-a]pyrimidin-4-one

14

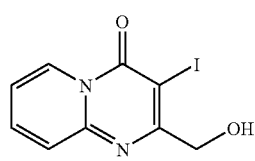

A mixture of 16.5 g (48.0 mmol) of the product from Step 3 (13) and 13.3 g (96.0 mmol) of potassium carbonate in 300 mL of methanol was stirred at ambient temperature for 3 hours. Excess water was added to the reaction mixture and the mixture was extracted using ethyl acetate (3×). The organic layers were combined, dried over MgSO₄ and activated carbon, and the solvent was removed in vacuo yielding 12 g (39.7 mmol, 83%) of 2-(hydroxymethyl)-3-iodo-4H-pyrido[1,2-a] pyrimidin-4-one as a white solid (14).

Step 5. 3-Benzyl-2-(hydroxymethyl)-4H-pyrido [1,2-a]pyrimidin-4-one

15

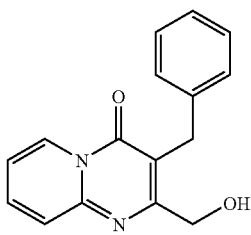

A mixture of 4.0 g (13.24 mmol) of the product from Step 4 (14), 1.0 g (1.32 mmol) of dichloro[1,1'-bis(diphenylphosphino)ferrocene] palladium(II) dichloromethane adduct, and 8.4 g (39.72 mmol) of K₃PO₄ in 30 mL of DMF was heated to 80° C. To the resulting solution was added dropwise 40 mL (19.9 mmol) of B-Benzyl-9-BBN and stirred at 80° C. under nitrogen for 12 hours. The reaction was then cooled to 0° C. and excess 1N NaOH was added to the reaction mixture. Excess 30% H₂O₂ was then added to the mixture at 0° C. resulting in significant gas evolution. Stirring continued for at least one additional hour or until gas ceased to evolve. The mixture was extracted with ethyl acetate (3×) and washed with saturated Na₂O₃S₂ and brine. The organic layers were combined, dried over MgSO₄ and activated carbon, and the solvent was removed in vacuo. The resulting material was subjected to flash chromatography on a 10 cm column. Elution with a gradient of 100% hexanes, 20% ethyl acetate in hexanes, 33% ethyl acetate in hexanes, 43% ethyl acetate in hexanes, 50% ethyl acetate in hexanes, 57% ethyl acetate in hexanes, 67% ethyl acetate in hexanes, and 100% ethyl acetate yielded 3.2 g (12.0 mmol, 91%) of 3-benzyl-2-(hydroxymethyl)-4H-pyrido[1,2-a]pyrimidin-4-one (15) as a pale yellow solid.

Step 6. 3-Benzyl-4-oxo-4H-pyrido[1,2-a]pyrimidine-2-carbaldehyde

16

26.5 mL (53.0 mmol) of oxalyl chloride in 40 mL dichloromethane was cooled to −78° C. To the resulting solution was added a solution of 7.52 mL (105.9 mmol) of DMSO in 24 mL dichloromethane and stirred at −78° C. for one hour. Then was added a solution of 4.7 g (17.65 mmol) of product from Step 5 (15) in 60 mL dichloromethane and the resulting mixture was stirred at −78° C. for one hour. Then was added 24.6 mL (176.5 mmol) of triethylamine and stirred at −78° C. for one hour. The mixture was then allowed to warm to 0° C. and stirred for another hour. Finally, the mixture was allowed to warm to ambient temperature over the course of one hour. Excess water was added to the reaction mixture and the mixture was extracted (3×) using dichloromethane. The combined organic layers were dried over MgSO$_4$ and activated carbon and the solvent was removed in vacuo. The resulting material was subjected to flash chromatography on a 10 cm column. Elution with a gradient of 100% hexanes, 20% ethyl acetate in hexanes, 33% ethyl acetate in hexanes, 43% ethyl acetate in hexanes, and 50% ethyl acetate in hexanes yielded 3.1 g (11.7 mmol, 67%) of 3-benzyl-4-oxo-4H-pyrido[1,2-a]pyrimidine-2-carbaldehyde (16) as a yellow solid.

Step 7. 3-Benzyl-2-(1-hydroxyprop-2-enyl)-6,7,8,9-tetrahydro-4H-pyrido[1,2-a]pyrimidin-4-one

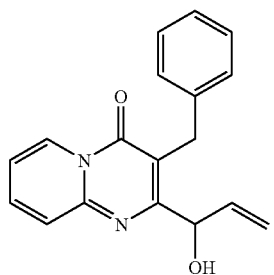

23

A mixture of 2.5 g (9.5 mmol) of the product from Step 6 (16) in 35 mL THF was cooled to −78° C. To the resulting solution was added dropwise 11.4 mL (11.4 mmol) of vinyl magnesium bromide and stirred at −78° C. for 3 hours. The reaction was quenched with saturated NH$_4$Cl and extracted with ethyl acetate (4×). The combined organic layers were dried over MgSO$_4$ and the solvent was removed in vacuo yielding 2.95 g of 3-benzyl-2-(1-hydroxyprop-2-enyl)-6,7,8,9-tetrahydro-4H-pyrido[1,2-a]pyrimidin-4-one (23) as a yellow oil.

Step 8. 3-Benzyl-2-(1-hydroxypropyl)-6,7,8,9-tetrahydro-4H-pyrido[1,2-a]pyrimidin-4-one

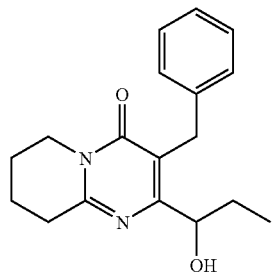

24

A mixture of 0.097 g (0.33 mmol) of the product from Step 7 (23) and 0.02 g of Palladium on activated carbon was stirred in 5 mL of ethyl acetate. The flask was equipped with a balloon containing hydrogen gas and the reaction mixture was stirred at ambient temperature for 3 days. The reaction mixture was then filtered through celite and washed with ethyl acetate. The resulting organic mixture was concentrated yielding 0.084 g (0.28 mmol, 85%) of 3-benzyl-2-(1-hydroxypropyl)-6,7,8,9-tetrahydro-4H-pyrido[1,2-a]pyrimidin-4-one (24) as a clear oil.

Step 9. 1-(3-Benzyl-4-oxo-6,7,8,9-tetrahydro-4H-pyrido[1,2-a]pyrimidin-2-yl)propyl methanesulfonate

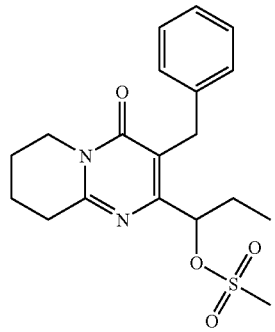

25

A mixture of 0.084 g (0.28 mmol) of the product (24) from Step 8 and 0.08 mL (0.56 mmol) of triethylamine in 2.5 mL of anhydrous DCM was cooled to 0° C. Then was added dropwise 0.03 mL (0.34 mmol) of methanesulfonyl chloride and the resulting mixture was allowed to warm to ambient temperature under nitrogen. Excess DCM was added and the reaction mixture was washed with water, saturated NaHCO₃ and brine. The organic layer was then dried over MgSO₄ and the solvent was removed in vacuo yielding 0.106 g (0.28 mmol, 100%) of 1-(3-benzyl-4-oxo-6,7,8,9-tetrahydro-4H-pyrido[1,2-a]pyrimidin-2-yl)propyl methanesulfonate (25) as a tan oil.

Step 10. Tert-butyl 3-{[1-(3-benzyl-4-oxo-6,7,8,9-tetrahydro-4H-pyrido [1,2-a]pyrimidin-2-yl)propyl]amino}propylcarbamate

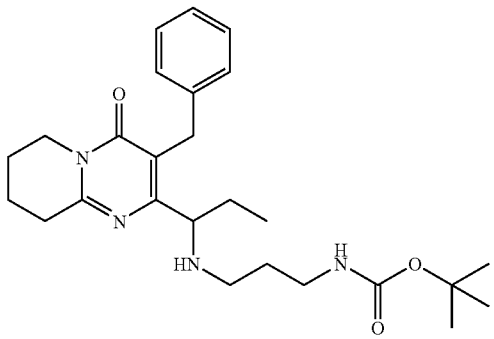

26

A mixture of 0.106 g (0.28 mmol) of the product from Step 9 (25), 0.15 g (0.84 mmol) of tert-butyl 3-aminopropylcarbamate, and 0.005 g (0.03 mmol) of potassium iodide in 5 mL of DMF was stirred at 60° C. under nitrogen for 24 hours. The reaction was quenched with water, extracted with ethyl acetate (4×) and the combined organic layers were washed with saturated NaHCO₃ and brine and dried over MgSO₄. The solvent was removed in vacuo and the crude reaction mixture was subjected to flash chromatography on a 7 cm column. Elution with a gradient of 50% ethyl acetate in hexanes, 100% ethyl acetate, 3% methanol and 0.1% ammonia in DCM, and 10% methanol and 0.1% ammonia in DCM yielded 0.019 g (0.04 mmol, 15%) of tert-butyl 3-{[1-(3-benzyl-4-oxo-6,7,8,9-tetrahydro-4H-pyrido[1,2-a]pyrimidin-2-yl)propyl]amino}propylcarbamate (26) as a clear oil.

Step 11. Tert-butyl 3-[[1-(3-benzyl-4-oxo-6,7,8,9-tetrahydro-4H-pyrido [1,2-a]pyrimidin-2-yl)propyl](4-bromobenzoyl)amino]propylcarbamate

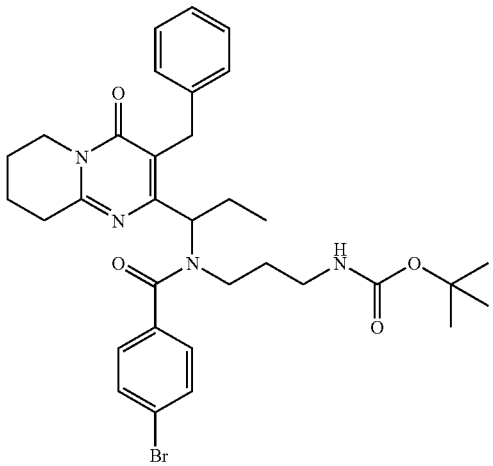

27

A mixture of 0.019 g (0.04 mmol) of the product from Step 10 (26), 0.0005 g (0.004 mmol) of DMAP, and 0.02 mL (0.12 mmol) of triethylamine in 2 mL anhydrous DCM was cooled to 0° C. Then was added 0.03 g (0.12 mmol) of 4-bromobenzoyl chloride and the resulting mixture was allowed to warm to ambient temperature under nitrogen. After 3 hours, the solvent was removed in vacuo and the resulting mixture was subjected to flash chromatography on a 5 cm column. Elution with a gradient of 20% ethyl acetate in hexanes, 33% ethyl acetate in hexanes, 50% ethyl acetate in hexanes, 66% ethyl acetate in hexanes, and 100% ethyl acetate yielded 0.013 g (0.02 mmol, 50%) of tert-butyl 3-[[1-(3-benzyl-4-oxo-6,7,8,9-tetrahydro-4H-pyrido[1,2-a]pyrimidin-2-yl)propyl](4-bromobenzoyl)amino]propylcarbamate (27) as a clear oil.

Step 12. N-(3-Aminopropyl)-N-[1-(3-benzyl-4-oxo-6,7,8,9-tetrahydro-4H-pyrido[1,2-a]pyrimidin-2-yl)propyl]-4-bromobenzamide

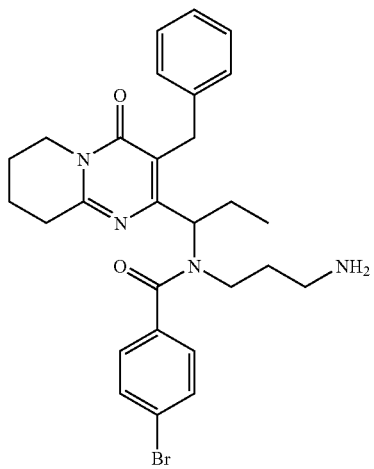

1

0.013 g (0.02 mmol) of the product from Step 11(27) in 0.1 mL trifluoroacetic acid and 1 mL DCM was stirred at ambient temperature for 2 hours. The solvent was the removed in vacuo yielding 0.0058 g (0.01, 50%) of N-(3-aminopropyl)-N-[1-(3-benzyl-4-oxo-6,7,8,9-tetrahydro-4H-pyrido[1,2-a]pyrimidin-2-yl)propyl]-4-bromobenzamide (1) as a white solid.

Example 3

Synthesis of N-(3-methylaminopropyl)-N-[1-(3-benzyl-4-oxo-6,7,8,9-tetrahydro-4H-pyrido[1,2-a]pyrimidin-2-yl)-2-methylpropyl]-4-methylbenzamide

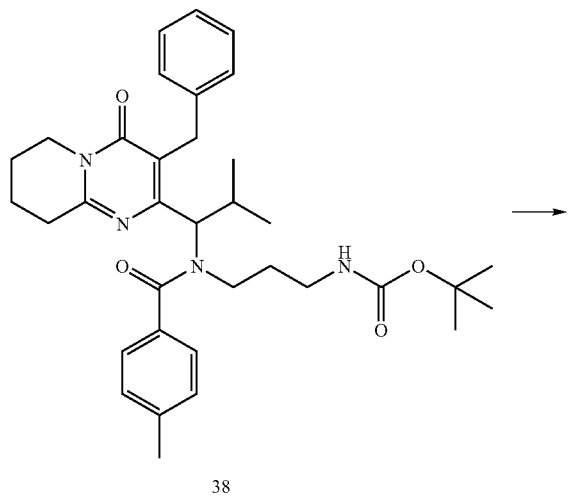

38

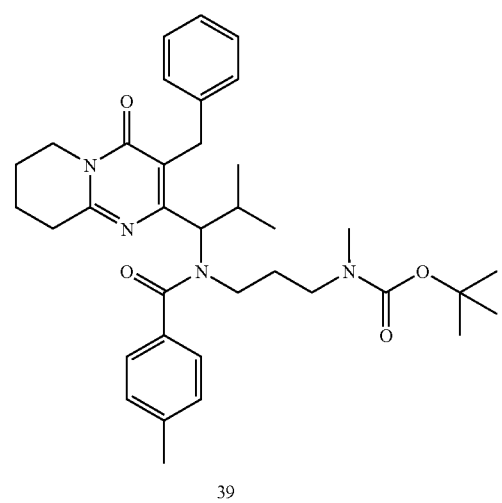

39

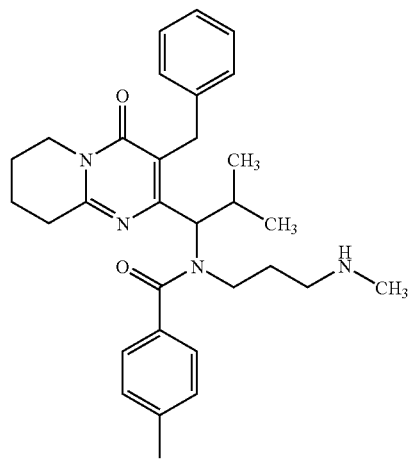

7

Compound 38 was synthesized using a protocol similar to the procedures detailed in step 11 of example 2.

To a flame dried reaction vial was added 0.015 g (0.026 mmol) compound 38, 0.002 mL (0.032 mmol), and 1 mL DMF and cooled to 0° C. Then 0.001 g (0.042 mmol) was added and the reaction was allowed to warm to ambient temperature under nitrogen for 1.5 hours. The reaction was then quenched with $H_2O$, extracted with $CH_2Cl_2$ (3×) and the combined organic layers were washed with saturated $NaHCO_3$ and brine, dried over $MgSO_4$ and the solvent was removed in vacuo. The resulting crude material was subjected to flash column chromatography and the product was eluted with a gradient of hexanes, 20% ethyl acetate in hexanes, 50% ethyl acetate in hexanes, and ethyl acetate yielding 0.01 g (0.017 mmol, 65%) Compound 39 as a clear oil.

Removal of the boc-group was done by conventional means to yield the title product 7.

The compounds in the table below were prepared using the methodology described in the previous examples. The starting materials used in the synthesis are recognizable to one of skill in the art and are commercially available or may be prepared using known methods. The compounds were named using ACD/Name Batch Version 5.04 (Advanced Chemistry Development, Inc.; Toronto Ontario).

| No. | Structure | MH+ | Name |
|---|---|---|---|
| 1 | 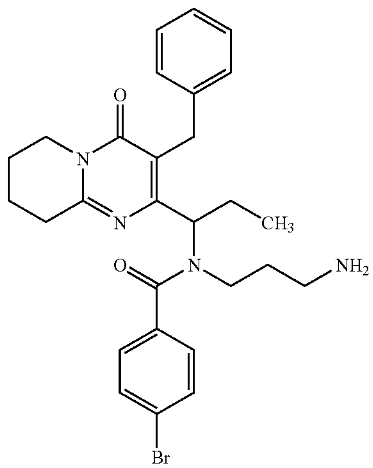 | 539.3 | N-(3-aminopropyl)-N-[1-(3-benzyl-4-oxo-6,7,8,9-tetrahydro-4H-pyrido[1,2-a]pyrimidin-2-yl)propyl]-4-bromobenzamide |
| 2 | 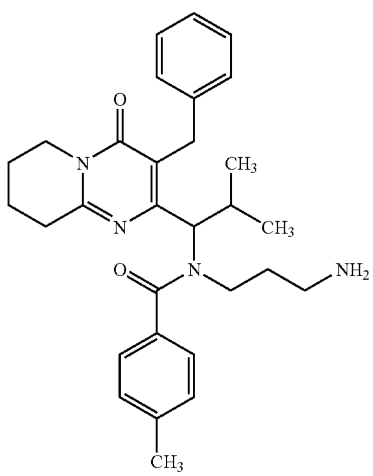 | 487.1 | N-(3-aminopropyl)-N-[1-(3-benzyl-4-oxo-6,7,8,9-tetrahydro-4H-pyrido[1,2-a]pyrimidin-2-yl)-2-methylpropyl]-4-methylbenzamide |
| 3 | 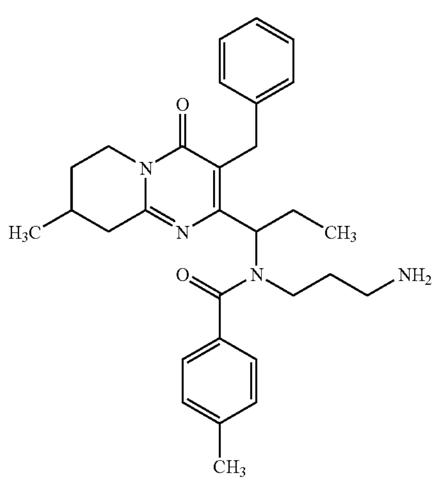 | 487.2 | N-(3-aminopropyl)-N-[1-(3-benzyl-8-methyl-4-oxo-6,7,8,9-tetrahydro-4H-pyrido[1,2-a]pyrimidin-2-yl)propyl]-4-methylbenzamide |

-continued

| No. | Structure | MH+ | Name |
|---|---|---|---|
| 4 | 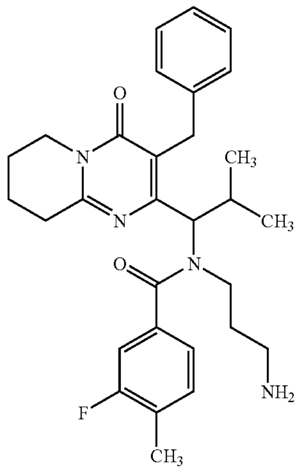 | 505.2 | N-(3-aminopropyl)-N-[1-(3-benzyl-4-oxo-6,7,8,9-tetrahydro-4H-pyrido[1,2-a]pyrimidin-2-yl)-2-methylpropyl]-3-fluoro-4-methylbenzamide |
| 5 | 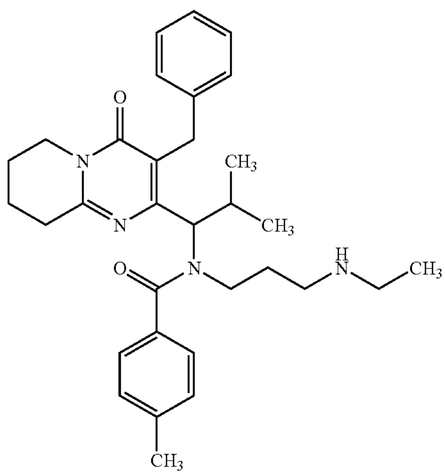 | 515.2 | N-(3-ethylaminopropyl)-N-[1-(3-benzyl-4-oxo-6,7,8,9-tetrahydro-4H-pyrido[1,2-a]pyrimidin-2-yl)-2-methylpropyl]-4-methylbenzamide |
| 6 | 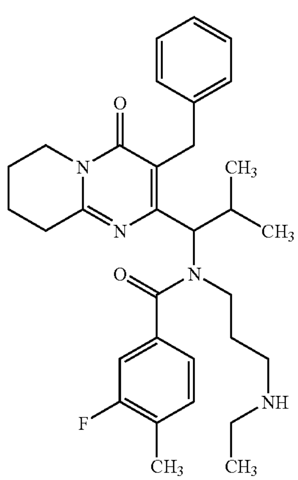 | 533.3 | N-(3-ethylaminopropyl)-N-[1-(3-benzyl-4-oxo-6,7,8,9-tetrahydro-4H-pyrido[1,2-a]pyrimidin-2-yl)-2-methylpropyl]-3-fluoro-4-methylbenzamide |

| No. | Structure | MH+ | Name |
|---|---|---|---|
| 7 | 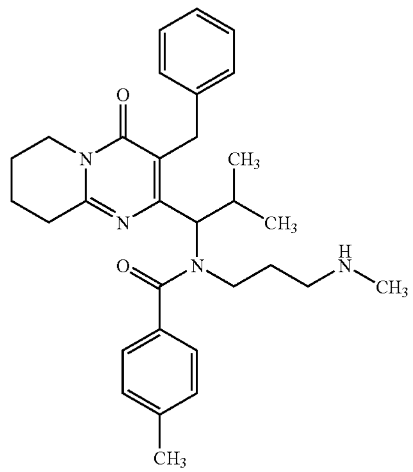 | 501.2 | N-(3-methylaminopropyl)-N-[1-(3-benzyl-4-oxo-6,7,8,9-tetrahydro-4H-pyrido[1,2-a]pyrimidin-2-yl)-2-methylpropyl]-4-methylbenzamide |

Example 4

Assay for Determining KSP Activity

This example provides a representative in vitro assay for determining KSP activity in vitro. Purified microtubules obtained from bovine brain were purchased from Cytoskeleton Inc. (Denver, Colo., USA). The motor domain of human KSP (Eg 5, KNSL1) was cloned, expressed, and purified to greater than 95% homogeneity. Biomol Green was purchased from Affinity Research Products Ltd. (Matford Court, Exeter, Devon, United Kingdom). Microtubules and KSP motor protein (i.e., the KSP motor domain) were diluted in assay buffer (20 mM Tris-HCl (pH 7.5), 1 mM MgCl$_2$, 10 mM DTT and 0.25 mg/ml BSA) to a final concentration of 35 µg/ml microtubules and 45 nM KSP. The microtubule/KSP mixture was then pre-incubated at 37° C. for 10 min to promote the binding of KSP to microtubules.

To each well of the testing plate (384-well plate) containing 1.25 µl of inhibitor or test compound in DMSO (or DMSO only in the case of controls) were added 25 µl of ATP solution (ATP diluted to a concentration of 300 µM in assay buffer) and 25 µl of the above-described microtubule/KSP solution. The plates were incubated at room temperature for 1 hour. Following incubation, 65 µl of Biomol Green (a malachite green-based dye that detects the release of inorganic phosphate) was added to each well. The plates were incubated for an additional 5-10 minutes then the absorbance at 630 nm was determined using a Victor II plate reader. The amount of absorbance at 630 nm corresponded to the amount of KSP activity in the samples. The IC50 of each inhibitor or test compound was then determined based on the decrease in absorbance at 630 nm at each concentration, via nonlinear regression using either XLFit for Excel or Prism data analysis software by GraphPad Software Inc.

The invention claimed is:

1. A compound of the formula:

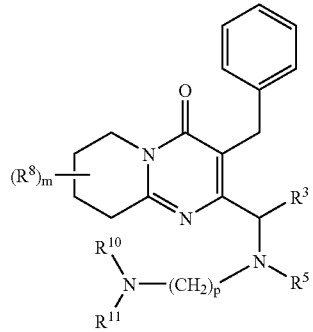

wherein:
m is 0, 1, 2, or 3;
p is 1,2,3 or 4;
$R^3$ is selected from the group consisting of alkyl, alkenyl, alkynyl, aryl, and heterocyclyl;
$R^5$ is selected from the group consisting of hydrogen, alkyl, aryl, heterocyclyl, alkoxycarbonyl, aryloxycarbonyl, heterocyclyloxycarbonyl, aminocarbonyl, alkylcarbonyl, arylcarbonyl, heterocyclylcarbonyl, alkylsulfonyl, arylsulfonyl, and heterocyclylsulfonyl
$R^8$ is selected from the group consisting of unsubstituted alkyl, substituted alkyl, aryl, and heterocyclyl;
$R^{10}$ and $R^{11}$ are independently selected from the group consisting of hydrogen and $C_1$ to $C_4$ alkyl;
wherein, said compound inhibits kinesin spindle protein with an IC$_{50}$ value of less than or equal to 25 µM;
or pharmaceutically acceptable salts or stereoisomers thereof.

2. The compound of claim 1 wherein when $R^3$ is alkyl, then alkyl is selected from the group consisting of —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH₂CH₂CH(CH₂CH₃)₂, —CH₂CH₂C(CH₃)₃, —CH₂CH₂C(CH₂CH₃), —CH(CH₃)CH₂CH(CH₃)₂, —CH(CH₃)CH(CH₃)CH(CH₃)₂, and —CH(CH₂CH₃)CH(CH₃)CH(CH₃)(CH₂CH₃).

3. The compound of claim 1, wherein $R^{10}$ and $R^{11}$ are hydrogen.

4. The compound of claim 1, wherein one of $R^{10}$ or $R^{11}$ is hydrogen and other is alkyl.

5. The compound of claim 1, wherein one of $R^{10}$ or $R^{11}$ is hydrogen and other is ethyl or methyl.

6. The compound of claim 1, wherein the $IC_{50}$ value of the compound is less than or equal to 10 μM.

7. The compound of claim 1, wherein the $IC_{50}$ value of the compound is less than or equal to 1 μM.

8. The compound of claim 1, wherein $R^3$ is selected from the group consisting of ethyl, isopropyl, cyclopropyl, phenyl, thienyl, and pyridinyl.

9. The compound of claim 8, wherein $R^3$ is ethyl or isopropyl.

10. The compound of claim 1, wherein $R^5$ is arylcarbonyl or heterocyclylcarbonyl.

11. The compound of claim 10, wherein $R^5$ is selected from the group consisting of benzoyl, 4-chlorobenzoyl, 4-bromobenzoyl, 4-methylbenzoyl, 4-trifluoromethylbenzoyl, and 3-fluoro-4-methylbenzoyl.

12. The compound of claim 11, wherein $R^5$ is selected from the group consisting of 4-bromobenzoyl, 4-methylbenzoyl and 3-fluoro-4-methylbenzoyl.

13. The compound of claim 1, wherein $R^8$ is unsubstituted alkyl or substituted alkyl.

14. The compound of claim 13, wherein $R^8$ is methyl.

15. The compound of claim 1, wherein m is 0 or 1.

16. The compound of claim 1, wherein p is 3.

17. A compound selected from the group consisting of:

N-(3-aminopropyl)-N-[1-(3-benzyl-4-oxo-6,7,8,9-tetrahydro-4H-pyrido[1,2-a]pyrimidin-2-yl)propyl]-4-bromobenzamide;

N-(3-aminopropyl)-N-[1-(3-benzyl-4-oxo-6,7,8,9-tetrahydro-4H-pyrido[1,2-a]pyrimidin-2-yl)-2-methylpropyl]-4-methylbenzamide;

N-(3-aminopropyl)-N-[1-(3-benzyl-8-methyl-4-oxo-6,7,8,9-tetrahydro-4H-Pyrido[1,2-a]pyrimidin-2-yl)propyl]-4-methylbenzamide;

N-(3-aminopropyl)-N-[1-(3-benzyl-4-oxo-6,7,8,9-tetrahydro-4H-pyrido[1,2-a]pyrimidin-2-yl)-2-methylpropyl]-3-fluoro-4-methylbenzamide;

N-(3-ethylaminopropyl)-N-[1-(3-benzyl-4-oxo-6,7,8,9-tetrahydro-4H-pyrido[1,2-a]pyrimidin-2-yl)-2-methylpropyl]-4-methylbenzamide;

N-(3-ethylaminopropyl)-N-[1-(3-benzyl-4-oxo-6,7,8,9-tetrahydro-4H-pyrido[1,2-a]pyrimidin-2-yl)-2-methylpropyl]-3-fluoro-4-methylbenzamide; and N-(3-methylaminopropyl)-N-[1-(3-benzyl-4-oxo-6,7,8,9-tetrahydro-4H-pyrido[1,2-a]pyrimidin-2-yl)-2-methylpropyl]-4-methylbenzamide.

18. A pharmaceutical composition comprising a therapeutically effective amount of a compound of claim 1 and a pharmaceutically acceptable carrier.

* * * * *